(12) United States Patent
Jensen et al.

US011844720B2

(10) Patent No.: US 11,844,720 B2
(45) Date of Patent: Dec. 19, 2023

(54) METHOD AND SYSTEM TO REDUCE THE LIKELIHOOD OF DENTAL CARIES AND HALITOSIS

(71) Applicant: SEED HEALTH, INC., Venice, CA (US)

(72) Inventors: Tye Jensen, Telluride, CO (US); Joseph E. Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 0 days.

(21) Appl. No.: 18/103,768

(22) Filed: Jan. 31, 2023

(65) Prior Publication Data

US 2023/0165706 A1    Jun. 1, 2023

Related U.S. Application Data

(63) Continuation-in-part of application No. 17/738,771, filed on May 6, 2022, which is a continuation-in-part of application No. 16/904,056, filed on Jun. 17, 2020, now Pat. No. 11,523,934, which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, said application No. 17/738,771 is a continuation-in-part of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671, said application No. 17/738,771 is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, said application No. 17/738,771 is a continuation-in-part of application No. 15/228,454, filed on Aug. 4, 2016, now Pat. No. 9,585,920, and a continuation-in-part of application No. 14/611,458, filed on Feb. 2, 2015, now Pat. No. 10,398,209, which is a continuation of application No. 14/502,097, filed on Sep. 30, 2014, now Pat. No. 9,010,340, which is a continuation of application No. 14/307,651, filed on Jun. 18, 2014, now Pat. No. 8,936,030, which is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 62/387,405, filed on Dec. 24, 2015, provisional application No. 61/439,652, filed on Feb. 4, 2011, provisional application No. 61/556,023, filed on Nov. 4, 2011, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 61/467,767, filed on Mar. 25, 2011, provisional application No. 62/387,404, filed on Dec. 24, 2015, provisional application No. 62/274,550, filed on Jan. 4, 2016, provisional application No. 62/275,341, filed on Jan. 6, 2016.

(51) Int. Cl.
*A61F 5/56*    (2006.01)

(52) U.S. Cl.
CPC ................................ *A61F 5/566* (2013.01)

(58) Field of Classification Search
None
See application file for complete search history.

(56) References Cited

U.S. PATENT DOCUMENTS

| | | |
|---|---|---|
| 1,492,600 A | 5/1924 | Laskey |
| 3,178,341 A | 4/1965 | Hamill et al. |
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |

(Continued)

FOREIGN PATENT DOCUMENTS

| | | |
|---|---|---|
| DE | 4412190 | 10/1995 |
| EP | 410696 | 1/1991 |

(Continued)

OTHER PUBLICATIONS

U.S. Appl. No. 17/854,389, filed Jun. 30, 2022, Kovarik.

(Continued)

*Primary Examiner* — Brian Gangle
(74) *Attorney, Agent, or Firm* — Sheridan Ross P.C.

(57) ABSTRACT

A method to facilitate the growth of desired bacteria in a human's mouth to reduce the likelihood of dental caries and halitosis and other oral diseases, and for inhibiting oral biofilm formation, gingivitis, periodontitis and halitosis via the employment of one or more probiotic bacterial, bioactive flavonoid, and zinc compound compositions effective in providing prevention and treatment options.

20 Claims, 4 Drawing Sheets

(56) References Cited

U.S. PATENT DOCUMENTS

| | | |
|---|---|---|
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,568,639 A | 2/1986 | Lew |
| 4,572,832 A | 2/1986 | Kigasawa et al. |
| 4,668,232 A | 5/1987 | Cordes et al. |
| 4,687,841 A | 8/1987 | Spilburg et al. |
| 4,713,243 A | 12/1987 | Schiraldi et al. |
| 4,715,369 A | 12/1987 | Susuki et al. |
| 4,720,486 A | 1/1988 | Spilburg et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,995,555 A | 2/1991 | Woodruff |
| 5,002,970 A | 3/1991 | Eby, III |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,277,877 A | 1/1994 | Jeffrey et al. |
| 5,284,161 A | 2/1994 | Karell |
| 5,298,258 A | 3/1994 | Akemi et al. |
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,518,733 A | 5/1996 | Lamothe et al. |
| 5,578,315 A | 11/1996 | Chien et al. |
| 5,585,098 A | 12/1996 | Coleman |
| 5,614,501 A | 3/1997 | Richards |
| 5,629,003 A | 5/1997 | Horstmann et al. |
| 5,643,603 A | 7/1997 | Bottenberg et al. |
| 5,700,478 A | 12/1997 | Biegajski et al. |
| 5,713,852 A | 2/1998 | Anthony et al. |
| 5,718,702 A | 2/1998 | Edwards |
| 5,719,196 A | 2/1998 | Uhari et al. |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |
| 5,855,872 A | 1/1999 | Libin |
| 5,876,995 A | 3/1999 | Bryan |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya et al. |
| 6,250,307 B1 | 6/2001 | Conrad et al. |
| 6,284,235 B1 | 9/2001 | Foreman et al. |
| 6,287,610 B1 | 9/2001 | Bowling et al. |
| 6,352,711 B1 | 3/2002 | Campbell |
| 6,375,963 B1 | 4/2002 | Repka et al. |
| 6,390,096 B1 | 5/2002 | Conrad et al. |
| 6,431,174 B1 | 8/2002 | Knudson et al. |
| 6,432,986 B2 | 8/2002 | Levin |
| 6,439,238 B1 | 8/2002 | Brenzel et al. |
| 6,453,905 B1 | 9/2002 | Conrad et al. |
| 6,458,380 B1 | 10/2002 | Leaderman |
| 6,458,777 B1 | 10/2002 | Sonis et al. |
| 6,467,485 B1 | 10/2002 | Schmidt |
| 6,502,574 B2 | 1/2003 | Stevens et al. |
| 6,509,028 B2 | 1/2003 | Williams et al. |
| 6,523,542 B2 | 2/2003 | Knudson et al. |
| 6,552,024 B1 | 4/2003 | Chen et al. |
| 6,555,125 B2 | 4/2003 | Campbell |
| 6,569,474 B2 | 5/2003 | Clayton et al. |
| 6,578,580 B2 | 6/2003 | Conrad et al. |
| 6,585,997 B2 | 7/2003 | Moro et al. |
| 6,599,883 B1 | 7/2003 | Romeo et al. |
| 6,620,846 B1 | 9/2003 | Jonn et al. |
| 6,713,463 B2 | 3/2004 | Sonis et al. |
| 6,722,577 B2 | 4/2004 | Dobyns, III |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrell et al. |
| 7,097,853 B1 | 8/2006 | Garbe et al. |
| 7,122,198 B1 | 10/2006 | Singh et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,267,975 B2 | 9/2007 | Strobel et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,353,194 B1 | 4/2008 | Kerker et al. |
| 7,357,891 B2 | 4/2008 | Yang et al. |
| 7,425,292 B2 | 9/2008 | Yang et al. |
| 7,441,559 B2 | 10/2008 | Nelson et al. |
| 7,470,397 B2 | 12/2008 | Meathrel et al. |
| 7,500,484 B2 | 3/2009 | Nelson et al. |
| 7,540,432 B2 | 6/2009 | Majerowski et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan et al. |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,820,420 B2 | 10/2010 | Whitlock |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,862,808 B2 | 1/2011 | Isolauri et al. |
| 7,901,925 B2 | 3/2011 | Bojrab |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,030,457 B2 | 10/2011 | Jackson et al. |
| 8,034,601 B2 | 10/2011 | Boileau et al. |
| 8,034,606 B2 | 10/2011 | Park et al. |

(56) References Cited

U.S. PATENT DOCUMENTS

| | | |
|---|---|---|
| 8,104,478 B2 | 1/2012 | Pflueger et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,383,201 B2 | 2/2013 | Berry et al. |
| 8,420,074 B2 | 4/2013 | Rehberger et al. |
| 8,454,729 B2 | 6/2013 | Mittelmark et al. |
| 8,481,299 B2 | 7/2013 | Gueniche et al. |
| 8,496,914 B2 | 7/2013 | Bonfiglio |
| 8,584,685 B2 | 11/2013 | Kovarik et al. |
| 8,585,588 B2 | 11/2013 | Kovarik et al. |
| 8,591,412 B2 | 11/2013 | Kovarik et al. |
| 8,657,879 B2 | 2/2014 | Shalon et al. |
| 8,685,389 B2 | 4/2014 | Baur et al. |
| 8,701,671 B2 | 4/2014 | Kovarik |
| 8,716,327 B2 | 5/2014 | Zhao et al. |
| 8,757,173 B2 | 6/2014 | Kovarik et al. |
| 8,758,764 B2 | 6/2014 | Masignani et al. |
| 8,815,538 B2 | 8/2014 | Lanzalaco et al. |
| 8,829,165 B2 | 9/2014 | Jackson et al. |
| 8,859,741 B2 | 10/2014 | Jackson et al. |
| 8,865,211 B2 | 10/2014 | Tzannis et al. |
| 8,936,030 B2 | 1/2015 | Kovarik et al. |
| 8,945,839 B2 | 2/2015 | Zhang et al. |
| 8,951,775 B2 | 2/2015 | Castiel et al. |
| 8,999,372 B2 | 4/2015 | Davidson et al. |
| 9,010,340 B2 | 4/2015 | Kovarik et al. |
| 9,011,834 B1 | 4/2015 | McKenzie et al. |
| 9,016,221 B2 | 4/2015 | Brennan et al. |
| 9,017,718 B2 | 4/2015 | Tan et al. |
| 9,028,841 B2 | 5/2015 | Henn et al. |
| 9,044,420 B2 | 6/2015 | Dubensky, Jr |
| 9,045,547 B2 | 6/2015 | Jackson et al. |
| 9,056,912 B2 | 6/2015 | Grandi et al. |
| 9,095,704 B2 | 8/2015 | McGuire et al. |
| 9,131,884 B2 | 9/2015 | Holmes et al. |
| 9,149,429 B2 | 10/2015 | Kovacs et al. |
| 9,234,204 B2 | 1/2016 | Qvit-Raz et al. |
| 9,254,295 B2 | 2/2016 | Adams et al. |
| 9,288,981 B2 | 3/2016 | Gandhi et al. |
| 9,295,682 B2 | 3/2016 | Nunes et al. |
| 9,314,489 B2 | 4/2016 | Kelly et al. |
| 9,445,936 B2 | 9/2016 | Kovarik |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 9,795,641 B2 | 10/2017 | Nardelli et al. |
| 9,987,224 B2 | 6/2018 | Kovarik et al. |
| 10,085,938 B2 | 10/2018 | Kovarik et al. |
| 10,086,018 B2 | 10/2018 | Kovarik |
| 10,111,913 B2 | 10/2018 | Kovarik |
| 10,195,273 B2 | 2/2019 | Clube |
| 10,245,288 B2 | 4/2019 | Kovarik |
| 10,314,865 B2 | 6/2019 | Kovarik |
| 10,314,866 B2 | 6/2019 | Kovarik |
| 10,512,661 B2 | 12/2019 | Kovarik |
| 10,548,761 B2 | 2/2020 | Kovarik |
| 10,555,976 B2 | 2/2020 | Kovarik |
| 10,668,014 B2 | 6/2020 | Kovarik et al. |
| 10,683,323 B2 | 6/2020 | Prakash et al. |
| 10,687,975 B2 | 6/2020 | Kovarik et al. |
| 10,716,815 B2 | 7/2020 | Kovarik et al. |
| 10,730,827 B2 | 8/2020 | Wortmann et al. |
| 10,760,075 B2 | 9/2020 | Sommer et al. |
| 10,835,560 B2 | 11/2020 | Kovarik |
| 10,940,169 B2 | 3/2021 | Kovarik et al. |
| 11,026,982 B2 | 6/2021 | Kovarik |
| 11,083,760 B2 | 8/2021 | Han |
| 11,213,552 B2 | 1/2022 | Kovarik |
| 11,357,722 B2 | 6/2022 | Kovarik et al. |
| 11,523,934 B2 | 12/2022 | Kovarik et al. |
| 11,529,379 B2 | 12/2022 | Kovarik |
| 2002/0009520 A1 | 1/2002 | Clayton et al. |
| 2002/0022057 A1 | 2/2002 | Battey et al. |
| 2002/0037310 A1 | 3/2002 | Jonn et al. |
| 2002/0044988 A1 | 4/2002 | Fuchs et al. |
| 2003/0031737 A1 | 2/2003 | Rosenbloom |
| 2003/0062050 A1 | 4/2003 | Schmidt |
| 2003/0083287 A1 | 5/2003 | Burgess et al. |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2003/0206995 A1 | 11/2003 | Bowling et al. |
| 2004/0053352 A1 | 3/2004 | Ouyang et al. |
| 2004/0057962 A1 | 3/2004 | Timmerman |
| 2004/0096569 A1 | 5/2004 | Barkalow et al. |
| 2004/0110111 A1 | 6/2004 | Wasylucha |
| 2004/0115223 A1 | 6/2004 | Follansbee |
| 2004/0120991 A1 | 6/2004 | Gardner et al. |
| 2004/0136923 A1 | 7/2004 | Davidson et al. |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0180080 A1 | 9/2004 | Furasawa et al. |
| 2004/0224007 A1 | 11/2004 | Zhang |
| 2004/0228804 A1 | 11/2004 | Jones et al. |
| 2005/0004417 A1 | 1/2005 | Nelson et al. |
| 2005/0159637 A9 | 1/2005 | Nelson et al. |
| 2005/0118655 A1 | 6/2005 | Weinstock et al. |
| 2005/0137109 A1 | 6/2005 | Quan et al. |
| 2005/0196358 A1 | 9/2005 | Georgiades et al. |
| 2005/0260544 A1 | 11/2005 | Jones et al. |
| 2006/0018843 A1 | 1/2006 | Fine |
| 2006/0035008 A1 | 2/2006 | Virgallito et al. |
| 2006/0064903 A1 | 3/2006 | Tucker |
| 2006/0127330 A1 | 6/2006 | Tsuchida et al. |
| 2006/0188813 A1 | 8/2006 | Shimada |
| 2006/0204591 A1 | 9/2006 | Burrel et al. |
| 2006/0207721 A1 | 9/2006 | Slominski et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis et al. |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0093420 A1 | 4/2007 | Yeomans et al. |
| 2007/0098744 A1 | 5/2007 | Knorr et al. |
| 2007/0102010 A1 | 5/2007 | Lemperle et al. |
| 2007/0122455 A1 | 5/2007 | Myers et al. |
| 2007/0123448 A1 | 5/2007 | Kaplan et al. |
| 2007/0148136 A1 | 6/2007 | Whitlock |
| 2007/0202057 A1 | 8/2007 | Fankhauser et al. |
| 2007/0207955 A1 | 9/2007 | Tanihara et al. |
| 2007/0218114 A1 | 9/2007 | Duggan |
| 2007/0227545 A1 | 10/2007 | Conrad et al. |
| 2007/0231923 A1 | 10/2007 | Cumberland et al. |
| 2007/0246052 A1 | 10/2007 | Hegde et al. |
| 2007/0261701 A1 | 11/2007 | Sanders |
| 2007/0280964 A1 | 12/2007 | Knorr et al. |
| 2007/0293587 A1 | 12/2007 | Haley |
| 2007/0295340 A1 | 12/2007 | Buscemi |
| 2008/0032253 A1 | 2/2008 | Montgomery et al. |
| 2008/0075825 A1 | 3/2008 | Fuisz et al. |
| 2008/0112983 A1 | 5/2008 | Bufe et al. |
| 2008/0242543 A1 | 10/2008 | Banerjee et al. |
| 2008/0267933 A1 | 10/2008 | Ohlson et al. |
| 2008/0286210 A1 | 11/2008 | He et al. |
| 2008/0305089 A1 | 12/2008 | Bufe et al. |
| 2009/0004275 A1 | 1/2009 | Martyn et al. |
| 2009/0098192 A1 | 4/2009 | Fuisz |
| 2009/0130199 A1 | 5/2009 | Kovacs et al. |
| 2009/0148482 A1 | 6/2009 | Peters |
| 2009/0196907 A1 | 8/2009 | Bunick et al. |
| 2009/0196908 A1 | 8/2009 | Lee et al. |
| 2009/0205083 A1 | 8/2009 | Gupta et al. |
| 2010/0029832 A1 | 2/2010 | Pinnavaia et al. |

(56) References Cited

U.S. PATENT DOCUMENTS

| | | |
|---|---|---|
| 2010/0040593 A1 | 2/2010 | Hedman et al. |
| 2010/0040712 A1 | 2/2010 | Fisher |
| 2010/0081681 A1 | 4/2010 | Blagosklonny |
| 2010/0092406 A1 | 4/2010 | Perez-Davidi et al. |
| 2010/0143447 A1 | 6/2010 | Hansen et al. |
| 2010/0229876 A1 | 9/2010 | Knudson et al. |
| 2010/0247644 A1 | 9/2010 | Domb et al. |
| 2010/0260720 A1 | 10/2010 | Sprenger |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Schobel et al. |
| 2011/0217368 A1 | 9/2011 | Prakash et al. |
| 2011/0230587 A1 | 9/2011 | MacInnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2011/0290694 A1 | 12/2011 | Fuisz et al. |
| 2012/0027786 A1 | 2/2012 | Gupta et al. |
| 2012/0029832 A1 | 2/2012 | Dodgson |
| 2012/0039806 A1 | 2/2012 | Lahoud et al. |
| 2012/0058094 A1 | 3/2012 | Blaser et al. |
| 2012/0128597 A1 | 5/2012 | Peters et al. |
| 2012/0142548 A1 | 6/2012 | Corsi et al. |
| 2012/0148629 A1 | 6/2012 | Holvoet et al. |
| 2012/0276143 A1 | 11/2012 | O'Mahony et al. |
| 2012/0276149 A1 | 11/2012 | Littman et al. |
| 2012/0276525 A1 | 11/2012 | Kovarik et al. |
| 2012/0283269 A1 | 11/2012 | Blagosklonny et al. |
| 2012/0294822 A1 | 11/2012 | Russo et al. |
| 2012/0301452 A1 | 11/2012 | Gueniche et al. |
| 2013/0059815 A1 | 3/2013 | Fournell et al. |
| 2013/0087155 A1 | 4/2013 | Hedman et al. |
| 2013/0157876 A1 | 6/2013 | Lynch et al. |
| 2013/0225440 A1 | 8/2013 | Friedman et al. |
| 2013/0236488 A1 | 9/2013 | Dashper et al. |
| 2013/0252983 A1 | 9/2013 | Cerione et al. |
| 2013/0259834 A1 | 10/2013 | Klaenhammer et al. |
| 2013/0310416 A1 | 11/2013 | Blagosklonny |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon et al. |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0125550 A1 | 5/2014 | Kaneko et al. |
| 2014/0154290 A1 | 6/2014 | Peters et al. |
| 2014/0199266 A1 | 7/2014 | Park et al. |
| 2014/0255351 A1 | 9/2014 | Berstad et al. |
| 2014/0271867 A1 | 9/2014 | Myers et al. |
| 2014/0294915 A1 | 10/2014 | Barreca et al. |
| 2014/0296139 A1 | 10/2014 | Cohen et al. |
| 2014/0333003 A1 | 11/2014 | Allen et al. |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0017143 A1 | 1/2015 | Holvoet et al. |
| 2015/0017227 A1 | 1/2015 | Kim et al. |
| 2015/0038594 A1 | 2/2015 | Borges et al. |
| 2015/0045546 A1 | 2/2015 | Siksnys et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0093473 A1 | 4/2015 | Barrangou et al. |
| 2015/0132263 A1 | 5/2015 | Liu et al. |
| 2015/0147371 A1 | 5/2015 | Kovarik et al. |
| 2015/0150792 A1 | 6/2015 | Klingman |
| 2015/0166641 A1 | 6/2015 | Goodman et al. |
| 2015/0174178 A1 | 6/2015 | Kovarik et al. |
| 2015/0190435 A1 | 7/2015 | Henn et al. |
| 2015/0202136 A1 | 7/2015 | Lanzalaco et al. |
| 2015/0216917 A1 | 8/2015 | Jones et al. |
| 2015/0224072 A1 | 8/2015 | Pellikaan |
| 2015/0252358 A1 | 9/2015 | Maeder et al. |
| 2015/0259728 A1 | 9/2015 | Cutliffe et al. |
| 2015/0329555 A1 | 11/2015 | Liras et al. |
| 2015/0329875 A1 | 11/2015 | Gregory et al. |
| 2015/0352023 A1 | 12/2015 | Berg et al. |
| 2015/0353901 A1 | 12/2015 | Liu et al. |
| 2015/0361436 A1 | 12/2015 | Hitchcock et al. |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Akins et al. |
| 2016/0069921 A1 | 3/2016 | Holmes et al. |
| 2016/0089315 A1 | 3/2016 | Kleinberg et al. |
| 2016/0089405 A1 | 3/2016 | Lue |
| 2016/0095316 A1 | 4/2016 | Goodman et al. |
| 2016/0120915 A1 | 5/2016 | Blaser et al. |
| 2016/0122806 A1 | 5/2016 | Amini et al. |
| 2016/0151427 A1 | 6/2016 | Whitlock et al. |
| 2016/0151428 A1 | 6/2016 | Bryan |
| 2016/0158294 A1 | 6/2016 | Von Maltzahn et al. |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206564 A1 | 7/2016 | Trachtman |
| 2016/0206666 A1 | 7/2016 | Falb et al. |
| 2016/0206668 A1 | 7/2016 | Kort et al. |
| 2016/0213702 A1 | 7/2016 | Von Maltzahn et al. |
| 2016/0243132 A1 | 8/2016 | Adams et al. |
| 2016/0271106 A1 | 9/2016 | Shi et al. |
| 2016/0271189 A1 | 9/2016 | Cutcliffe et al. |
| 2016/0311913 A1 | 10/2016 | Sun et al. |
| 2016/0314281 A1 | 10/2016 | Apte et al. |
| 2016/0354416 A1 | 12/2016 | Gajewski et al. |
| 2016/0374941 A1 | 12/2016 | Barreca et al. |
| 2017/0014341 A1 | 1/2017 | Armer et al. |
| 2017/0020932 A1 | 1/2017 | Cutcliffe et al. |
| 2017/0027914 A1 | 2/2017 | Qi |
| 2017/0042860 A1 | 2/2017 | Kashyap et al. |
| 2017/0042924 A1 | 2/2017 | Otsuka et al. |
| 2017/0071986 A1 | 3/2017 | Kovarik et al. |
| 2017/0079947 A1 | 3/2017 | Richards |
| 2017/0100328 A1 | 4/2017 | Kovarik et al. |
| 2017/0232043 A1 | 8/2017 | Falb et al. |
| 2017/0240625 A1 | 8/2017 | Zeller et al. |
| 2017/0246269 A1 | 8/2017 | Hajishengallis et al. |
| 2017/0298115 A1 | 10/2017 | Loomis et al. |
| 2017/0312232 A1 | 11/2017 | Vitetta et al. |
| 2017/0342141 A1 | 11/2017 | Russo et al. |
| 2017/0348303 A1 | 12/2017 | Bosse et al. |
| 2018/0000878 A1 | 1/2018 | Goodman et al. |
| 2018/0015131 A1 | 1/2018 | Gajewski et al. |
| 2018/0016647 A1 | 1/2018 | Van Sinderen et al. |
| 2018/0092899 A1 | 4/2018 | Liu et al. |
| 2018/0100169 A1 | 4/2018 | Soucaille et al. |
| 2018/0110795 A1 | 4/2018 | Frias-Lopez |
| 2018/0111984 A1 | 5/2018 | Bigal et al. |
| 2018/0127490 A1 | 5/2018 | Bigal et al. |
| 2018/0134772 A1 | 5/2018 | Sharma et al. |
| 2018/0140698 A1 | 5/2018 | Clube et al. |
| 2018/0207165 A1 | 7/2018 | Harmsen et al. |
| 2018/0235987 A1 | 8/2018 | Von Maltzahn et al. |
| 2018/0258100 A1 | 9/2018 | Gregory et al. |
| 2018/0296582 A1 | 10/2018 | von Maltzahn et al. |
| 2018/0303658 A1 | 10/2018 | Kovarik et al. |
| 2018/0312851 A1 | 11/2018 | Falb et al. |
| 2018/0326008 A1 | 11/2018 | Schreiber et al. |
| 2018/0371405 A1 | 12/2018 | Barrangou et al. |
| 2019/0000815 A1 | 1/2019 | Melin |

(56) References Cited

U.S. PATENT DOCUMENTS

| | | |
|---|---|---|
| 2019/0018012 A1 | 1/2019 | Kovarik |
| 2019/0059314 A1 | 2/2019 | Aharoni et al. |
| 2019/0290605 A1 | 6/2019 | Rasochova et al. |
| 2019/0120960 A1 | 7/2019 | Konradi et al. |
| 2019/0262298 A1 | 8/2019 | Kanthasamy et al. |
| 2019/0315642 A1 | 10/2019 | Parsley et al. |
| 2019/0388471 A1 | 12/2019 | June et al. |
| 2019/0390284 A1 | 12/2019 | Kim |
| 2020/0009185 A1 | 1/2020 | Shin et al. |
| 2020/0009268 A1 | 1/2020 | Scholz |
| 2020/0032224 A1 | 1/2020 | Schaefer et al. |
| 2020/0121743 A1 | 4/2020 | Kovarik |
| 2020/0148642 A1 | 5/2020 | Konradi et al. |
| 2020/0155447 A1 | 5/2020 | Edwards |
| 2020/0163796 A1 | 5/2020 | Kovarik |
| 2020/0188454 A1 | 6/2020 | Slykerman |
| 2020/0190494 A1 | 6/2020 | Hou et al. |
| 2020/0197215 A1 | 6/2020 | Kovarik et al. |
| 2020/0199555 A1 | 6/2020 | Zhang |
| 2020/0397832 A1 | 12/2020 | Kovarik |
| 2021/0000883 A1 | 1/2021 | Kovarik |
| 2021/0169954 A1 | 6/2021 | Balani et al. |
| 2021/0198665 A1 | 7/2021 | Sommer et al. |
| 2021/0308028 A1 | 10/2021 | Yang et al. |
| 2021/0321756 A1 | 10/2021 | McLaughlin et al. |
| 2021/0361560 A1 | 11/2021 | Krueger et al. |
| 2021/0386659 A1 | 12/2021 | Kim |
| 2022/0000760 A1 | 1/2022 | Rasochova |
| 2022/0023259 A1 | 1/2022 | Davidson et al. |
| 2022/0031590 A1 | 2/2022 | Pesaro et al. |
| 2022/0031767 A1 | 2/2022 | Duportet et al. |
| 2022/0071877 A1 | 3/2022 | Zenobia et al. |
| 2022/0088001 A1 | 3/2022 | Kovarik et al. |
| 2022/0088090 A1 | 3/2022 | Lobacki et al. |
| 2022/0118031 A1 | 4/2022 | Kovarik |
| 2022/0135987 A1 | 5/2022 | Leveau et al. |
| 2022/0193150 A1 | 6/2022 | Kovarik |
| 2022/0193157 A1 | 6/2022 | Zimmerman et al. |
| 2022/0257410 A1 | 8/2022 | Kovarik |
| 2022/0296500 A1 | 9/2022 | Kovarik |
| 2022/0331374 A1 | 10/2022 | Richter et al. |
| 2022/0331375 A1 | 10/2022 | Kovarik |
| 2022/0339208 A1 | 10/2022 | Abel et al. |
| 2022/0378853 A1 | 12/2022 | Kovarik |
| 2023/0106721 A1 | 4/2023 | Catania et al. |

FOREIGN PATENT DOCUMENTS

| | | |
|---|---|---|
| JP | S56-100714 | 8/1981 |
| WO | WO 98/22097 | 5/1998 |
| WO | WO 2006/007922 | 1/2006 |
| WO | WO 2006/015445 | 2/2006 |
| WO | WO 2006/133879 | 12/2006 |
| WO | WO 2008/088426 | 7/2008 |
| WO | WO 2008/097890 | 8/2008 |
| WO | WO 2009/052421 | 4/2009 |
| WO | WO 2010/041143 | 4/2010 |
| WO | WO 2011/020780 | 2/2011 |
| WO | WO 2011/029701 | 3/2011 |
| WO | WO 2013/026000 | 2/2013 |
| WO | WO 2013/107750 | 7/2013 |
| WO | WO 2013/182038 | 12/2013 |
| WO | WO 2014/103488 | 7/2014 |
| WO | WO 2014/182632 | 11/2014 |
| WO | WO 2014/196913 | 12/2014 |
| WO | WO 2015/069682 | 5/2015 |
| WO | WO 2016/070151 | 5/2016 |
| WO | WO 2017/211753 | 12/2017 |
| WO | WO 2019/067621 | 4/2019 |
| WO | WO 2022/187274 | 9/2022 |

OTHER PUBLICATIONS

U.S. Appl. No. 17/893,384, filed Aug. 23, 2022, Kovarik.
U.S. Appl. No. 18/087,545, filed Dec. 22, 2022, Kovarik.
"Oral Cavity," University of Michigan Medical School, Date Unknown, retrieved Nov. 20, 2019 from https://histology.medicine.umich.edu/resources/oral-cavity, 5 pages.
"The structure behind the simplicity of CRISPR/Cas9," The Scinder at Medium.com, Dec. 23, 2015, retrieved from https://medium.com/the-scinder/the-structure-behind-the-simplicity-of-crispr-cas9-6f8cb60695c4, 8 pages.
Abruzzo et al., "Influence of Lactobacillus Biosurfactants on Skin Permeation of Hydrocortisone," Pharmaceutics, vol. 13, No. 6, May 2021, 14 pages.
Agrawal et al., "Technique to Control pH in Vicinity of Biodegrading PLA-PGA Implants," Journal of Biomedical Materials Research, vol. 38, No. 2, 1997, pp. 105-114.
Aguilar-Toala et al., "Potential role of natural bioactive peptides for development of cosmeceutical skin products," Peptides, vol. 122, No. 170170, Dec. 2019, 8 pages. Abstract only.
Athanasiou et al., "In Vitro Degradation and Release Characteristics of Biodegradable Implants Containing Trypsin Inhibitor," Clinical Orthopaedics and Related Research, vol. 315, Jun. 1995, pp. 272-281. Abstract only.
Basseri et al., "Antibiotics for the Treatment of Irritable Bowel Syndrome," Gastroenterology & Hepatology, vol. 7, No. 7, Jul. 2011, pp. 455-493.
Blumen et al., "Radiofrequency Ablation for the Treatment of Mild to Moderate Obstructive Sleep Apnea," The Laryngoscope, vol. 112, No. 11, Nov. 2002, pp. 2086-2092.
Bocheva et al., "Protective Role of Melatonin and Its Metabolites in Skin Aging," International Journal of Molecular Sciences, vol. 23, No. 1238, Jan. 2022, 23 pages.
Brietzke et al., "Injection Snoreplasty: Extended Follow-Up and New Objective Data," Otolaryngology—Head and Neck Surgery, vol. 128, No. 5, May 2003, pp. 605-615. Abstract only.
Brietzke et al., "Injection Snoreplasty: How to Treat Snoring without All the Pain and Expense," Otolaryngology—Head and Neck Surgery, vol. 124, No. 5, May 2001, pp. 503-510. Abstract only.
Brietzke et al., "Injection Snoreplasty: Investigation of Alternative Sclerotherapy Agents," Otolaryngology—Head and Neck Surgery, vol. 130, No. 1, Jan. 2004, pp. 47-57. Abstract only.
Catalano et al., "Additional palatal implants for refractory snoring," Otolaryngology—Head and Neck Surgery, vol. 137, No. 1, Jul. 2007, pp. 105-109. Abstract only.
Charulatha et al., "Influence of different crosslinking treatments on the physical properties of collagen membranes," Biomaterials, vol. 24, No. 5, 2003, pp. 759-767.
Chen et al., "Targeting Aldehyde Dehydrogenase 2: New Therapeutic Opportunities," Physiological Reviews, vol. 94, No. 1, 2014, 65 pages.
Choi et al., "Therapeutic Effects of Cold-Pressed Perilla Oil Mainly Consisting of Linolenic acid, Oleic Acid and Linoleic Acid on UV-Induced Photoaging in NHDF Cells and SKH-1 Hairless Mice," Molecules, vol. 25, Feb. 2020, 19 pages.
Chuang et al., "Effects of exogenous crosslinking on in vitro tensile and compressive moduli of lumbar intervertebral discs," Clinical Biomechanics, vol. 22, No. 1, Jan. 2007, pp. 14-20. Abstract only.
Courage, "Fiber-Famished Gut Microbes Linked to Poor Health," Scientific American, Mar. 23, 2015, retrieved from https://www.scientificamerican.com/article/fiber-famished-gut-microbes-linked-to-poor-health, 10 pages.
Ding et al., "Resveratrol accelerates wound healing by inducing M2 macrophage polarisation in diabetic mice," Pharmaceutical Biology, vol. 60, No. 1, 2022, pp. 2328-2337.
Douam et al., "Genetic Dissection of the Host Tropism of Human-Tropic Pathogens," Annual Review of Genetics, vol. 49, 2015, pp. 21-45.
Dunkley et al., "A role for CD4+ T cells from orally immunized rats in enhanced clearance of Pseudomonas aeruginosa from the lung," Immunology, vol. 83, 1994, pp. 362-369.
Earlia et al., "GC/MS Analysis of Fatty Acids on Pliek U Oil and Its Pharmacological Study by Molecular Docking to Filaggrin as a Drug Candidate in Atopic Dermatitis Treatment," Scientific World Journal, Nov. 2019, 7 pages.

(56) References Cited

OTHER PUBLICATIONS

Enomoto et al., "Koji amazake Maintains Water Content in the Left Cheek Skin of Healthy Adults: A Randomized, Double-Blind, Placebo-Controlled, Parallel-Group, Comparative Trial," Clinical, Cosmetic and Investigational Dermatology, vol. 15, Jul. 2022, pp. 1283-1291.

Farhadihosseinabadi et al., "The in vivo effect of Lacto-N-neotetraose (LNnT) on the expression of type 2 immune response involved genes in the wound healing process," Scientific Reports, vol. 10, No. 997, Jan. 2020, 11 pages.

Fischer et al., "[Radiofrequency ablation of the soft palate (somnoplasty). A new method in the treatment of habitual and obstructive snoring]," HNO, vol. 48, No. 1, Jan. 2000, pp. 33-40. Abstract only.

Friedman et al., "Patient Selection and Efficacy of Pillar Implant Technique for Treatment of Snoring and Obstructive Sleep Apnea/Hypopnea Syndrome," Otolaryngology—Head and Neck Surgery, vol. 134, No. 2, Feb. 2006, pp. 187-196. Abstract only.

Gratzer et al., "Control of pH Alters the Type of Cross-linking Produced by 1-Ethyl-3-(3-Dimethylaminopropyl)-Carbodiimide (EDC) Treatment of Acellular Matrix Vascular Grafts," Journal of Biomedical Materials Research, vol. 58, No. 2, 2001, pp. 172-179.

Guilleminault et al., "Snoring (I). Daytime sleepiness in regular heavy snorers," Chest, vol. 99, 1991, pp. 40-48.

Guilleminault et al., "The sleep apnea syndromes," Annual Review of Medicine, vol. 27, Feb. 1976, pp. 465-484. First Page Only.

Han et al., "Proanthocyanidin: A natural crosslinking reagent for stabilizing collagen matrices," Journal of Biomedical Materials Research, vol. 65A, No. 1, Apr. 2003, pp. 118-124. Abstract only.

Hedman et al., "Exogenous Cross-Linking Increases the Stability of Spinal Motion Segments," Spine, vol. 31, No. 15, Jul. 2006, pp. E480-E485. Abstract only.

Hoffmann et al., "Glutaraldehyde and oxidised dextran as crosslinker reagents for chitosan-based scaffolds for cartilage tissue engineering," Journal of Materials Science: Materials in Medicine, vol. 20, Mar. 2009, pp. 1495-1503.

Hunter et al., "Meniscal material properties are minimally affected by matrix stabilization using glutaraldehyde and glycation with ribose," Journal of Orthopaedic Research, vol. 23, 2005, pp. 555-561.

Kim et al., "Kaempferol tetrasaccharides restore skin atrophy via PDK1 inhibition in human skin cells and tissues: Bench and clinical studies," Biomedicine & Pharmacotherapy, vol. 156, No. 113864, Dec. 2022, 13 pages.

Kim et al., "Spermidine-induced recovery of human dermal structure and barrier function by skin microbiome," Communications Biology, vol. 4, No. 231, 2021, 11 pages.

Kim et al., "β-Glucogallin isolated from Fusidium coccineum and its enhancement of skin barrier effects," Applied Biological Chemistry, vol. 63, No. 77, Nov. 2020, 7 pages.

Klapperich et al., "A novel biocompatible adhesive incorporating plant-derived monomers," Journal of Biomedical Materials Research Part A, vol. 91, No. 2, pp. 378-374.

Klingspor et al., "Research Article: Enterococcus faecium NCIMB 10415 Modulates Epithelial Integrity, Heat Shock Protein, and Proinflammatory Cytokine Response in Intestinal Cells," Mediators of Inflammation, vol. 2015, No. 304149 ,2015, 12 pages.

Ko, "Effects of Glycogen on Ceramide Production in Cultured Human Keratinocytes via Acid Sphingomyelinase Activation," Master's Thesis Submitted to the Graduate School of Public Health (Korea), 2018, 53 pages.

Komuro et al., "Sphingomyelin maintains the cutaneous barrier via regulation of the STAT3 pathway," The FASEB Journal, vol. 36, No. 4, Apr. 2022, 17 pages.

Kurek-Gorecka et al., "Bee Products in Dermatology and Skin Care," Molecules, vol. 25, No. 3, Jan. 2020, 17 pages.

Kyriakopoulos et al., "Taurine and N-Bromotaurine in Topical Treatment of Psoriasis," Advances in Experimental Medicine and Biology, vol. 1370, 2022, pp. 99-111. Abstract only.

Laneri et al., "Plant cell culture extract of Cirsium eriophorum with skin pore refiner activity by modulating sebum production and inflammatory response," Phytotherapy Research, vol. 35, No. 1, Jan. 2021, pp. 530-540.

Lebeer et al., "Selective targeting of skin pathobionts and inflammation with topically applied lactobacilli," Cell Reports Medicine, vol. 3, No. 2, Feb. 2022, 22 pages.

Lew et al., "Bioactives from probiotics for dermal health: functions and benefits," Journal of Applied Microbiology, vol. 114, No. 5, May 2013, pp. 1241-1253.

Liu et al., "Activation of aryl hydrocarbon receptor in Langerhans cells by a microbial metabolite of tryptophan negatively regulates skin inflammation," Journal of Dermatological Science, vol. 100, No. 3, Dec. 2020, pp. 192-200. Abstract only.

Liu et al., "The potential of *Streptococcus thermophiles* (TCI633) in the anti-aging," Journal of Cosmetic Dermatology, vol. 21, No. 6, Jun. 2022, pp. 2635-2647.

Mach et al., "Endurance exercise and gut microbiota: A review," Journal of Sport and Health Science, vol. 6, No. 2, Jun. 2017, pp. 179-197.

Mahdiani et al., "Protective effect of luteolin against chemical and natural toxicants by targeting NF-κB pathway," Biofactors, vol. 48, No. 4, Jul. 2022, pp. 744-762. Abstract only.

Matsui et al., "Biological Rhythms in the Skin," International Journal of Molecular Sciences, vol. 17, No. 801, May 2016, 15 pages.

Mayrovitz et al., "Assessing Potential Circadian, Diurnal, and Ultradian Variations in Skin Biophysical Properties," Cureus, vol. 13, No. 9, Sep. 2021, 18 pages.

McFadzean, "Exercise can help modulate human gut microbiota," Honors Thesis Submitted to the University of Colorado Department of Evolutionary Biology, Apr. 7, 2014, 34 pages.

Nakai et al., "Effects of Topical N-Acetylcysteine on Skin Hydration/Transepidermal Water Loss in Healthy Volunteers and Atopic Dermatitis Patients," Annals of Dermatology, vol. 27, No. 4, Aug. 2015, pp. 450-451.

Neves et al., "Efficacy of a topical serum containing L-ascorbic acid, neohesperidin, pycnogenol, tocopherol, and hyaluronic acid in relation to skin aging signs," Journal of Cosmetic Dermatology, vol. 21, No. 10, Oct. 2022, pp. 4462-4469. Abstract only.

Nisbet et al., "Clinical and in vitro evaluation of new anti-redness cosmetic products in subjects with winter xerosis and sensitive skin," International Journal of Cosmetic Science, vol. 41, No. 6, Dec. 2019, pp. 534-547.

Park et al., "Fermented black rice and blueberry with Lactobacillus plantarum MG4221 improve UVB-induced skin injury," Food and Agricultural Immunology, vol. 32, No. 1, 2021, pp. 499-515.

Pinto et al., "Plantaricin A synthesized by Lactobacillus plantarum induces in vitro proliferation and migration of human keratinocytes and increases the expression of TGF-β1, FGF7, VEGF-A and IL-8 genes," Peptides, vol. 32, No. 9, Sep. 2011, pp. 1815-1824. Abstract only.

Ragusa et al., "Spirulina for Skin Care: A Bright Blue Future," Cosmetics, vol. 8, No. 1, Jan. 2021, 19 pages.

Sevilla et al., "Revisiting the role of melatonin in human melanocyte physiology: A skin context perspective," Journal of Pineal Research, vol. 72, No. 3, Apr. 2022, 23 pages.

Sheikh, "Is Crispr the Next Antibiotic?," The New York Times, Oct. 29, 2019, retrieved from https://www.nytimes.com/2019/28/health/crispr-genetics-antibiotic-resistance.html, 2 pages.

Shen et al., "Propionibacterium acnes related anti-inflammation and skin hydration activities of madecassoside, a pentacyclic triterpene saponin from Centella asiatica," Bioscience, Biotechnology, and Biochemistry, vol. 83, No. 3, 2019, pp. 561-568.

Sheweita et al., "Preclinical studies on melanogenesis proteins using a resveratrol-nanoformula as a skin whitener," International Journal of Biological Macromolecules, vol. 223, Part A, Dec. 2022, pp. 870-881. Abstract only.

Sivieri et al., "Lactobacillus acidophilus CRL 1014 improved "gut health" in the SHIME reactor," BMC Gastroenterology, vol. 13, No. 100, 2013, 9 pages.

(56) References Cited

OTHER PUBLICATIONS

Spinler et al., "Human-derived probiotic Lactobacillus reuteri demonstrate antimicrobial activities targeting diverse enteric bacterial pathogens," Anaerobe, vol. 14, Feb. 29, 2008, pp. 166-171.
Thongaram et al., "Human milk oligosaccharide consumption by probiotic and human-associated bifidobacteria and lactobacilli," Journal of Dairy Science, vol. 100, No. 10, Oct. 2017, pp. 7825-7833.
Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins, vol. 11, No. 6, May 2019, 12 pages.
Van Der Veer et al., "Comparative genomics of human Lactobacillus crispatus isolates reveals genes for glycosylation and glycogen degradation: implications for in vivo dominance of the vaginal microbiota," Microbiome, vol. 7, No. 49, 2019, 14 pages.
Van Hemert et al., "Migraine associated with gastrointestinal disorders: review of the literature and clinical implications," Frontiers in Neurology, vol. 5, No. 241, Nov. 2014, 4 pages.
Wan et al., "Luteolin-7-glucoside Promotes Human Epidermal Stem Cell Proliferation by Upregulating β-Catenin, c-Myc, and Cyclin Expression," Stem Cells International, vol. 2019, No. 1575480, Jun. 2019, 10 pages.
Wilbie et al., "Delivery Aspects of CRISPR/Cas for in Vivo Genome Editing," Accounts of Chemical Research, vol. 52, 2019, pp. 1555-1564.
Yamamura et al., "Oral mucosal adhesive Film containing local anesthetics: in vitro and clinical evaluation." Journal of Biomedical Materials Research, Fall 1998, vol. 43, No. 3, pp. 313-317. Abstract only.
Yatsuhashi et al., "Effects of Glycogen on Ceramide Production in Cultured Human Keratinocytes via Acid Sphingomyelinase Activation," Journal of Applied Glycoscience, vol. 68, 2021, pp. 41-46.
Yosipovitch et al., "Time-Dependent Variations of the Skin Barrier Function in Humans: Transepidermal Water Loss, Stratum Corneum Hydration, Skin Surface pH, and Skin Temperature," Journal of INvestigative Dermatology, vol. 110, No. 1, Jan. 1998, pp. 20-23.
Zahedi et al., "Development of plasma functionalized polypropylene wound dressing for betaine hydrochloride controlled drug delivery on diabetic wounds," Scientific Reports, vol. 11, No. 9641, 2021, 18 pages.
Zhou et al., "Nicotinamide Mononucleotide Combined With Lactobacillus fermentum TKSN041 Reduces the Photoaging Damage in Murine Skin by Activating AMPK Signaling Pathway," Frontiers in Pharmacology, vol. 12, No. 643089, Mar. 2021, 17 pages.
Official Action for U.S. Appl. No. 13/367,052, dated Jan. 16, 2014, 8 pages.
Notice of Allowance for U.S. Appl. No. 13/367,052, dated Feb. 24, 2014, 5 pages.
Official Action for U.S. Appl. No. 14/225,503, dated May 4, 2016, 6 pages.
Notice of Allowance for U.S. Appl. No. 14/225,503, dated Jul. 20, 2016, 5 pages.
Official Action for U.S. Appl. No. 14/752,192, dated Jul. 8, 2016, 8 pages.
Notice of Allowance for U.S. Appl. No. 14/752,192, dated Sep. 16, 2016, 5 pages.
Official Action for U.S. Appl. No. 15/378,425, dated May 15, 2019, 82 pages.
Official Action for U.S. Appl. No. 15/378,425, dated Oct. 2, 2019, 41 pages.
Official Action for U.S. Appl. No. 15/378,425, dated Jul. 15, 2020, 21 pages.
Official Action for U.S. Appl. No. 15/378,425, dated Nov. 10, 2020, 29 pages.
Official Action for U.S. Appl. No. 15/385,278, dated Oct. 30, 2017, 23 pages.
Official Action for U.S. Appl. No. 15/385,278, dated Apr. 13, 2018, 18 pages.
Notice of Allowance for U.S. Appl. No. 15/385,278, dated May 31, 2018, 10 pages.
Official Action for U.S. Appl. No. 16/136,950, dated Nov. 25, 2019, 11 pages.
Official Action for U.S. Appl. No. 16/136,950, dated Jan. 31, 2020, 8 pages.
Official Action for U.S. Appl. No. 16/884,772, dated Sep. 30, 2021, 8 pages.
Notice of Allowance for U.S. Appl. No. 16/884,772, dated Feb. 22, 2022, 7 pages.
Official Action for U.S. Appl. No. 15/384,716, dated Nov. 1, 2017, 31 pages.
Notice of Allowance for U.S. Appl. No. 15/384,716, dated Apr. 2, 2018, 9 pages.
Official Action for U.S. Appl. No. 15/983,250, dated Mar. 5, 2019, 23 pages.
Official Action for U.S. Appl. No. 15/983,250, dated May 24, 2019, 21 pages.
Official Action for U.S. Appl. No. 15/983,250, dated Jan. 14, 2020, 8 pages.
Notice of Allowance for U.S. Appl. No. 15/983,250, dated Feb. 14, 2020, 8 pages.
Official Action for U.S. Appl. No. 16/904,056, dated Dec. 6, 2021, 12 pages.
Official Action for U.S. Appl. No. 16/904,056, dated May 17, 2022, 11 pages.
Notice of Allowance for U.S. Appl. No. 16/094,056, dated Aug. 11, 2022, 8 pages.
Corrected Notice of Allowance for U.S. Appl. No. 16/904,056, dated Aug. 24, 2022, 6 pages.
Official Action for U.S. Appl. No. 15/403,823, dated Oct. 30, 2017, 7 pages.
Official Action for U.S. Appl. No. 15/403,823, dated May 25, 2018, 9 pages.
Notice of Allowance for U.S. Appl. No. 15/403,823, dated Jun. 28, 2018, 9 pages.
Official Action for U.S. Appl. No. 16/160,336, dated Nov. 27, 2018, 6 pages.
Notice of Allowance for U.S. Appl. No. 16/160,336, dated Feb. 15, 2019, 7 pages.
Official Action for U.S. Appl. No. 16/423,375, dated Jul. 3, 2019, 6 pages.
Notice of Allowance for U.S. Appl. No. 16/423,375, dated Oct. 16, 2019, 8 pages.
Official Action for U.S. Appl. No. 16/782,364, dated Apr. 9, 2020, 5 pages.
Notice of Allowance for U.S. Appl. No. 16/782,364, dated Jul. 27, 2020, 7 pages.
Official Action for U.S. Appl. No. 16/917,096, dated Jul. 31, 2020, 5 pages.
Official Action for U.S. Appl. No. 16/617,096, dated Oct. 19, 2020, 8 pages.
Official Action for U.S. Appl. No. 17/027,953, dated Jan. 29, 2021, 5 pages.
Notice of Allowance for U.S. Appl. No. 17/027,953, dated Apr. 19, 2021, 8 pages.
Official Action for U.S. Appl. No. 17/337,600, dated Jul. 6, 2021, 5 pages.
Notice of Allowance for U.S. Appl. No. 17/337,600, dated Sep. 9, 2021, 7 pages.
Official Action for U.S. Appl. No. 17/835,204, dated Jul. 28, 2022, 6 pages.
Notice of Allowance for U.S. Appl. No. 17/835,204, dated Aug. 24, 2022, 7 pages.
Official Action for U.S. Appl. No. 17/848,759, dated Sep. 14, 2022, 6 pages.
Notice of Allowance for U.S. Appl. No. 17/848,759, dated Dec. 29, 2022, 7 pages.
Corrected Notice of Allowance for U.S. Appl. No. 17/848,759, dated Jan. 12, 2023, 4 pages.
Official Action for U.S. Appl. No. 17/854,422, dated Sep. 28, 2022, 7 pages.

(56) References Cited

OTHER PUBLICATIONS

Official Action for U.S. Appl. No. 17/854,422, dated Jan. 10, 2023, 6 pages.
Notice of Allowance for U.S. Appl. No. 17/854,422, dated Feb. 17, 2023, 7 pages.
Auerbach et al., "Angiogenesis assays: Problems and pitfalls," Cancer and Metastasis Reviews, vol. 19, 2000, pp. 167-172.
Gura, "Systems for Identifying New Drugs Are Often Faulty," Science, vol. 278, No. 5340, Nov. 7, 1997, pp. 1041-1042.
Hennessy et al., "Statins as next generation anti-microbials: Is there potential for repurposing?," Antimicrob. Agents Chemother., Jun. 20, 2016, 46 pages.
Jain, "Barriers to Drug Delivery in Solid Tumors," Scientific American, Jul. 1994, pp. 58-65.
Kilkkinen et al., "Use of antimicrobials and risk of type 1 diabetes in a population-based mother-child cohort," Diabetologia, vol. 49, 2006, pp. 66-70.
Kimoto et al., "New Lactococcus Strain with Immunnomodulatory Activity: Enhancement of Th1-Type Immune Response," Microbiol. Immunol., vol. 48, No. 2, 2004, pp. 75-82.
Malaguarnera et al., "Bifidobacterium longum with Fructo-Oligosaccharides in Patients with Non Alcoholic Steatohepatitis," Digestive Diseases and Sciences, vol. 57, 2012, pp. 545-553.
Norton et al., "The immune response to Lactococcus lactis: Implications for its use as a vaccine delivery vehicle," FEMS Microbiology Letters, vol. 120, No. 3, Jul. 15, 1994, pp. 249-256. Abstract only.
Repa et al., "Mucosal co-application of lactic acid bacteria and allergen induces counter-regulatory immune responses in a murine model of birch pollen allergy," Vaccine, vol. 22, No. 1, 2003, pp. 87-95. Abstract only.
Sporn et al., "Chemoprevention of cancer," Carcinogenesis, vol. 21, No. 3, 2000, pp. 525-530.
Zhao et al., "Microbiome-generated amyloid and potential impact on amyloidogenesis in Alzheimer's disease (AD)," Journal of Nature and Science, vol. 1, No. 7, 2015, pp. 1-5.
Official Action for U.S. Appl. No. 14/574,517 dated Jan. 6, 2016, 13 pages.
Notice of Allowance for U.S. Appl. No. 14/574,517, dated Apr. 15, 2016, 8 pages.
Corrected Notice of Allowance for U.S. Appl. No. 14/574,517, dated Jul. 7, 2016, 2 pages.
Official Action for U.S. Appl. No. 14/954,074, dated Jun. 30, 2016, 4 pages.
Notice of Allowance for U.S. Appl. No. 14/954,074, dated Jul. 20, 2016, 7 pages.
Official Action for U.S. Appl. No. 15/270,034, dated Apr. 6, 2017, 5 pages.
Notice of Allowance for U.S. Appl. No. 15/270,034, dated May 5, 2017, 7 pages.
Official Action for U.S. Appl. No. 15/392,173, dated Jan. 22, 2018, 8 pages.
Official Action for U.S. Appl. No. 15/392,173, dated Jul. 6, 2018, 13 pages.
Notice of Allowance for U.S. Appl. No. 15/392,173, dated Dec. 5, 2018, 8 pages.
Official Action for U.S. Appl. No. 16/229,252, dated Feb. 28, 2019, 5 pages.
Notice of Allowance for U.S. Appl. No. 16/229,252, dated Aug. 21, 2019, 7 pages.
Official Action for U.S. Appl. No. 16/722,117, dated Feb. 20, 2020, 6 pages.
Notice of Allowance for U.S. Appl. No. 16/722,117, dated Jul. 30, 2020, 8 pages.
Official Action for U.S. Appl. No. 17/011,175, dated Jun. 17, 2021, 9 pages.
Notice of Allowance for U.S. Appl. No. 17/011,175, dated Nov. 5, 2021, 8 pages.
Official Action for U.S. Appl. No. 17/023,736, dated Nov. 10, 2021, 7 pages.
Notice of Allowance for U.S. Appl. No. 17/023,736, dated Apr. 14, 2022, 8 pages.
Official Action for U.S. Appl. No. 17/893,384, dated May 9, 2023, 8 pages.
Official Action for U.S. Appl. No. 18/087,545, dated May 24, 2023, 5 pages.
Official Action for U.S. Appl. No. 15/228,454, dated Sep. 23, 2016, 11 pages.
Notice of Allowance for U.S. Appl. No. 15/228,454, dated Jan. 23, 2017, 7 pages.
Official Action for U.S. Appl. No. 15/437,976, dated Mar. 29, 2017, 8 pages.
Notice of Allowance for U.S. Appl. No. 15/437,976, dated Jul. 12, 2017, 7 pages.
Official Action for U.S. Appl. No. 15/639,767, dated Aug. 14, 2017, 11 pages.
Official Action for U.S. Appl. No. 15/639,767, dated Sep. 27, 2018, 13 pages.
Notice of Allowance for U.S. Appl. No. 15/369,767, dated Feb. 15, 2019, 8 pages.
Official Action for U.S. Appl. No. 16/426,346, dated Aug. 2, 2019, 10 pages.
Official Action for U.S. Appl. No. 16/426,346, dated Jan. 13, 2020, 7 pages.
Notice of Allowance for U.S. Appl. No. 16/426,346, dated Mar. 25, 2020, 7 pages.

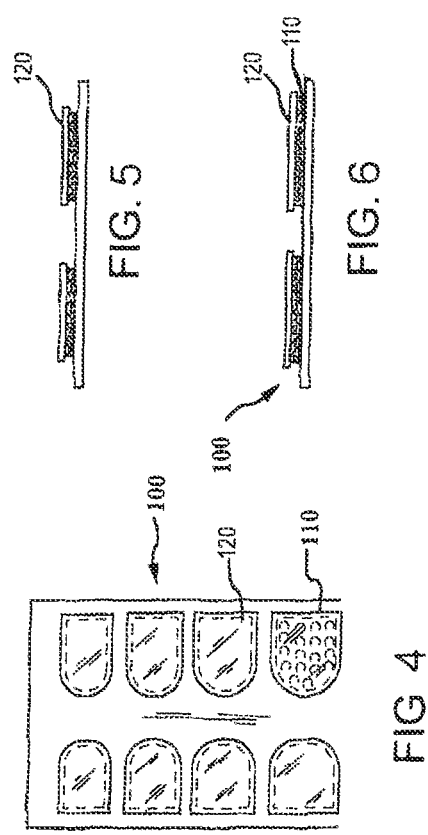

METHOD AND SYSTEM TO REDUCE THE LIKELIHOOD OF DENTAL CARIES AND HALITOSIS

RELATED APPLICATIONS

This application is a continuation-in-part of U.S. patent application Ser. No. 17/738,771, filed May 6, 2022, which is a continuation-in-part of U.S. patent application Ser. No. 16/904,056, filed Jun. 17, 2020 (now U.S. Pat. No. 11,523,934, issued Dec. 13, 2022), which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is a continuation-in-part application of U.S. patent application Ser. No. 14/752,192 filed Jun. 26, 2015 (now U.S. Pat. No. 9,549,842, issued Jan. 24, 2017), which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016 (now U.S. Pat. No. 9,585,920, issued Mar. 7, 2017), which claims priority of U.S. Provisional Patent Application Ser. Nos. 62/387,404, filed Dec. 24, 2015; 62/274,550, filed Jan. 4, 2016; and 62/275,341, filed Jan. 6, 2016.

This application is also a continuation-in-part application of U.S. patent application Ser. No. 14/611,458, filed Feb. 2, 2015 (now U.S. Pat. No. 10,398,209, issued Sep. 3, 2019), which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14/307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913, filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference.

FIELD OF THE INVENTION

A method to facilitate the growth of desired bacteria in a human's mouth to reduce the likelihood of dental caries and halitosis and other oral diseases, and for inhibiting oral biofilm formation, gingivitis, periodontitis and halitosis via the employment of one or more probiotic bacterial, bioactive flavonoid, and zinc compound compositions effective in providing prevention and treatment options.

BACKGROUND OF THE INVENTION

Dental plaque is a biofilm composed of a community of oral microbes that reside on the surface of the tooth. Oral bacteria act as binding sites for other bacteria, leading to the formation of plaque biofilms. Dental caries are caused by excess fermentable carbohydrates (for example, sugar) that are used by bacteria, such as *Streptococcus mutans*, to produce organic acids, which cause localized acidification that inhibits the growth of many health-associated bacteria. Such acidification and decreased microbial diversity creates a feedback loop which promotes further acidification of the local environment, leading to the demineralization of enamel and dentin and the creation of dental caries and tooth decay. Dental plaque is typically a sticky colorless film caused by bacterial deposits accumulating on tooth surfaces along the gingival margins that often results in the destruction of tooth-supporting tissues. Dental plaque formation starts in cracks, grooves and surface roughness on teeth and/or dental implants. In any given plaque sample, it is not uncommon to detect 30 or more bacterial species. Biofilms that colonize the tooth surface may be among the most complex biofilms that exist in nature.

Gingivitis is an inflammatory disease of the gums that can eventually lead to periodontitis, caused by a dysbiosis of the microbial community in the subgingival space, triggering a dysregulated and destructive inflammatory response in the host. Periodontitis is also linked to systemic health, with increased risk of adverse pregnancy outcomes, rheumatoid arthritis, atherosclerosis, autoimmune diseases, diabetes, and cancers. The destruction of tooth-supporting tissues results in a deepening of the space (periodontal pocket) between the root of the tooth and the gum tissue. Second to tooth decay, periodontal diseases are the most frequent oral diseases and may lead to partial or complete tooth or bone loss. It has been estimated that they affect as much as between 70-90% of the world population, and they are the major cause of tooth loss in people over 35 years of age. In periodontitis the infection has progressed to involve the oral tissues which retain the teeth in the jawbone. If untreated, periodontitis ultimately leads to loss of the affected tooth. Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase, finally causing spontaneous loss of a tooth or a necessity of tooth extraction. Treatment of periodontal diseases usually involves the removal of bacterial deposits and dental calculus. However, it is difficult to have full access for treating deeper periodontal pockets, resulting in remaining bacteria that may re-infect the tissue.

Periodontal diseases are infections caused by microorganisms that colonize the tooth or implant surface at or below the gingival margin. While these infections have many properties in common with other infectious diseases, they exhibit unique properties conferred by their site of colonization and the nature of the environment in which they reside. The onset of the diseases is usually delayed for prolonged periods of time after initial colonization by the pathogens.

Halitosis, or bad breath, is a term referring to an unpleasant or annoying odor that emanates from the oral cavity of an individual and affects between 30 and 50% of the population. Its main cause is the putrefaction of sulfur-containing amino acids, with hydrogen sulfide, methylmercaptan, and dimethylsulfide being the main culprits. Halitosis has a great psychological impact due to the social isolation it produces, being one of the conditions for which people seek dental care, after caries and periodontal disease. Halitosis is mainly attributed to biofilm accumulation on the dorsum of the tongue, interdental spaces, under orthodontic and orthopedic prostheses and appliances, and chronic inflammatory diseases of the periodontium. Halitosis is caused by volatile sulfur compounds produced by oral anaerobic bacteria, commonly residing on the tongue. Halitosis-associated bacteria include *Solobacterium moorei, P. gingivalis, Ta. forsythia, Bacteroides forsythus*, and *Treponema denticola*. Antibiotics kill microorganisms that are responsible for producing acid in the mouth, such as *Streptococcus mutans*, but antibiotics are not selective in the killing of oral bacteria and also kill beneficial bacteria present in the oral cavity. This can result in a microbial imbalance in the mouth, which can have serious consequences. There is a long felt but unsolved need for a method and system to reduce the likelihood of dental caries, for inhibiting biofilm formation, gingivitis, periodontitis and halitosis.

Oral conditions such as halitosis, a periodontal disease, or caries may be caused by a dysbiosis of microorganisms inhabiting the oral cavity. One or more bacterial species that are naturally occurring even in healthy individuals can become overly abundant to a point where those microorganisms reach pathogenic levels either in the entirety of the oral cavity or in isolated spaces, such as lesions or pockets between gum and tooth. To date, chemical or other invasive treatments such as mouth washes or dental procedures are used to treat or prevent oral diseases, such as gum disease or caries that may be caused by such bacteria. However, such methods are often invasive, have poor patient compliance, and do not discriminate between detrimental bacteria and beneficial bacteria and thus can result in even more severe disease states over time. Indeed, typical mouth washes and other chemicals intended to treat oral diseases (e.g., halitosis, periodontal disease, and/or caries) may indiscriminately kill all bacteria present in an oral microbiome (e.g., including bacteria that may form a healthy oral microbiome). One of the disadvantages of these conventional approaches is that their beneficial and/or therapeutic effect may only last for short periods of time. Moreover, conventional methods to treat oral diseases such as halitosis, periodontal disease, and/or caries may not hinder the regrowth of detrimental bacteria. Detrimental bacteria may be more likely to survive in protected sites, which may often correlate with sites of disease (e.g., periodontal pockets, cavities, or crevices on the tongue dorsum). This may cause an even greater overabundance of detrimental bacteria relative to beneficial bacteria.

There is a need to help individuals in reducing the likelihood of developing dental caries and halitosis and other undesired oral conditions by providing alternative and superior prevention and/or treatment options for oral diseases that address the root causes of such diseases rather than merely treating their symptoms.

SUMMARY OF THE INVENTION

Certain embodiments of the present invention are directed to a prophylactic method for reducing the likelihood of forming dental caries and/or treating dental caries, comprising administering (preferably directly after a professional dental cleaning, and/or after an antibiotic application and rinse thereof) a probiotic composition of bacteria designed to form a more healthy oral microbiome. Other aspects of the present are directed to combating halitosis, which is mainly caused by volatile sulfur compounds produced by oral anaerobes such as *Porphyromonas gingivalis, Fusobacterium nucleatum, Treponema denticola* and *Prevotella intermedia*. Certain embodiments of the present invention are directed to the oral administration of probiotic lactobacilli to improve halitosis. For example, in addition to other bacterial combinations, as well as preferred formulations with zinc compounds and flavonoids, bacteria such as *Bifidobacterium lactis* and *Lactobacillus acidophilus* may be employed to provide benefits in combating pathogens related to halitosis, perhaps related to inhibitory effect on the production and emission of malodorous compounds by such bacteria. One aspect of various embodiments of the present invention is directed to control plaque formation and prevent the breakdown of microbial homeostasis, acting on the maintenance and improvement of oral health, which also may lead to undesired malodors. Oral malodour is classified as either genuine halitosis, which includes both intraoral and extraoral and physiologic halitosis, known as transient, or nongenuine halitosis, which includes pseudo-halitosis and halitophobia. Lack of interdental cleaning plays a significant high incidence in oral malodor. Compounds that could contribute to the breath odor, including what is termed "morning breath"—include many volatile sulfur compounds, such as methanethiol, hydrogen sulfide, dimethyl sulfide, and 2-methyl-1-propanethiol, but also other VOCs, such as acetic acid, butyric acid, valeric acid, acetaldehyde, octanal, phenol, indole, ammonia, isoprene, and methyl methacrylate.

Within the oral cavity, bacteria form multispecies communities that are distinguishable primarily by their location (supragingival versus subgingival versus epithelial). The subgingival community has the highest species richness and the greatest capacity for pathogenic outcome, such as periodontal tissue destruction. Competitive and cooperative mechanisms may be central to successful mixed species colonization as well as the proper succession of genera known to occur on teeth in both health and disease.

Certain oral bacteria, unlike human cells, are able to reduce nitrate to nitrite effectively, leading to an increase in systemic nitrite, useful in treating a variety of diseases and conditions, including but not limited to oral health, hypertension and diabetes. Oral bacteria can also reduce nitrite to nitric oxide, a free radical with antimicrobial properties capable of inhibiting sensitive species such as anaerobes involved in periodontal diseases. The nitrate-reducing bacteria *Rothia* and *Neisseria* have been found at higher levels in individuals free of oral disease as compared to those with dental caries, periodontitis, or halitosis. In the presence of nitrate, certain oral bacteria decrease, such as *Veillonella* (caries) and *Prevotella* (periodontal diseases and halitosis). One aspect of the present invention is to increase nitrate in the oral cavity to increase health-associated, beneficial bacterial species populations and thereby provide the benefits of nitrate reduction on oral health.

Various embodiments of the present invention are directed to practices that establish and retain and maintain oral health such that individuals do not suffer from the array of different maladies that are now understood to be related, whether directly or indirectly, to oral health. When individuals to get their teeth cleaned a few times a year, the dental surfaces are relatively "clean" of the biofilms that where established thereon since the last dental cleaning visit. Instead of proactively applying a beneficial composition of beneficial bacteria to the cleaned surfaces, however, it is to leave the colonization of the dental surfaces up to the chance presence of bacteria that may then be present in the person's mouth or surrounding environments. Thus, one aspect of the present invention to purposefully contact a person's recently cleaned teeth with a composition that contains bacteria believed to be especially beneficial to the establishment of a "healthy" biofilm, some of which may include modified bacteria that lack one or more virulence facts, thus establishing a population of bacteria that can competitively inhibit the colonization of very similar species of bacteria given their securing a place in the biofilm from an earlier time period. Certain embodiments include a progressive and successive contact of a person's teeth with different bacteria, with the staging of contact with various bacteria based upon the known synergistic relationship between oral bacteria. Other embodiments are directed to limiting the most pathogenic bacteria known to cause some of the prevalent problems suffered by humans.

As bacteria belonging to the genus *Streptococcus* are the first inhabitants of the oral cavity that are acquired right after birth, they play an important role in the assembly of the oral microbiota. Oral streptococci produce many adhesive molecules to permit them to efficiently colonize surfaces in the oral cavity and have the ability to metabolize carbohydrates via fermentation to generate acids as byproducts. While acidification of the oral environment by aciduric species such as *Streptococcus mutans* is directly associated with the development of dental caries, less acid-tolerant species such as *Streptococcus salivarius* and *Streptococcus gordonii* produce large amounts of alkali, thereby playing an displaying and important role in the acid-base physiology of the oral cavity. Thus, certain aspects and embodiments of the present invention are directed towards the reduction in the likelihood of developing dental caries via the modification of the oral cavity microbiome so as to reduce the acidification required for *S. mutans* to cause caries, often involving encouraging the growth of *S. salivarius* bacterial populations. Still other embodiments involve the growth and maintenance of certain oral streptococci due to their ability to generate hydrogen peroxide so as to inhibit the growth of *S. mutans*.

In certain embodiments, virulence traits expressed by oral *E. faecalis* strains are modified, preferably via the CRISPR systems disclosed herein, so as to reduce the production of the virulence factors hemolysin and/or gelatinase. Gelatinase production of *E. faecalis* is an important factor for bacterial adhesion, and thus, reducing adherence abilities of such bacteria reduces the formation of undesired dental biofilms.

Provision of certain bacteria to form a desired biofilm is done either directly after a dental cleaning or by an individual at home, so as to establish a preferred buildup of a beneficial biofilm having particular bacteria constituents. Streptococci constitute 60 to 90% of the bacteria that colonize the teeth in the first 4 hours after professional cleaning. Other early colonizers include *Actinomyces* spp., *Capnocytophaga* spp., *Eikenella* spp., *Haemophilus* spp., *Prevotella* spp., *Propionibacterium* spp., and *Veillonella* spp. Such formulations for beneficial oral cavity health may vary dependent upon many factors, such as the particular diet of the individual, the race of the individual, the age, etc. It is known that bacterial populations vary greatly between individuals, as well as within the same individual based on health and age. Thus, selection of particular compositions having a pre-determined composition of bacteria formats and variety are contemplated by the present invention, such composition dictated by several parameters, including the above referenced ones, as well as provision of select sugars, such as xylitol. Certain aspects of the present invention are directed to the employment of orally administered compositions, preferably provided via oral strips that adhere to surfaces in the oral cavity and that include at least one of xylitol, *Lachnospira, Veillonella, Faecalibacterium* and/or *Rothia* bacteria.

The bacteria associated with periodontal diseases reside in biofilms both above and below the gingival margin. The supragingival biofilm is attached to the tooth or the implant and predominated by *Actinomyces* species. The subgingival biofilm is typically more complex and can either attach to the tooth or implant, or to the gingival tissue. Three microbe species are believed to be main players in the cause the periodontal diseases: *A. actinomycetemcomitans, P. gingivalis* and *B. forsythus*. Also, *F. nucleatum, Campylobacter rectus, P. Intermedia, P. nigrescens, Eubacterium nodatum, P. micros* and various spirochetes have been singled out that may also be important species in periodontal disease. As described herein, these, as well as other species, can be modified to, for example, remove one or more virulence factors to provide a biofilm that is less damaging than a biofilm would be that included such bacteria. In other words, certain embodiments are directed to modification of certain bacteria to enhance the ability of a collection of bacteria to form more healthy (or at least not as disease prone) biofilms, thereby enhancing the health of an individual.

Nitric oxide (NO) acts as environmental cues that trigger the coordinated expression of virulence genes and metabolic adaptations necessary for survival within a host. NO concentrations may be produced by microbiota from nitrate, with the nitrate being reduced to ammonium by the dissimilatory nitrate reduction to ammonium (DNRA) pathway. Salivary glands concentrate plasma nitrate into saliva, leading to high nitrate concentrations. Certain microbiota can generate substantial amounts of NO by DNRA, rather than by the generally accepted denitrification or L-arginine pathway. Bacterial nitrate reduction to ammonia as well as the related NO formation, is believed to be an important aspect of the overall mammalian nitrate/nitrite/NO metabolism, demonstrating how the microbiome links diet and health. The nitric oxide synthase inhibitor NG-monomethyi-L-arginine (L-NMMA) may be employed in several embodiments of the present invention. Nitric oxide synthases (NOSs) are multidomain metalloproteins first identified in mammals as being responsible for the synthesis of the wide-spread signaling and protective agent nitric oxide (NO). Nitric oxide synthases are heme-based monooxygenases that oxidize L-arginine to nitric oxide (NO), a signaling molecule and cytotoxic agent in higher organisms. NO is one of the main inflammatory mediators involved in both inflammation and angiogenesis. NO can be synthesized by three different isoforms of NO synthase: neuronal (nNOS), endothelial (eNOS), and inducible (iNOS) synthases. NO production due to cytokine-induced expression of inducible nitric oxide synthase (iNOS) is largely involved in the pathophysiology of inflammation.

Although NOS-like activity has been reported in many bacteria, only a few bacterial homologs of mammalian NOSs (mNOSs) have been characterized to date. Nitric oxide synthases (NOSs) play an essential role in synthesizing nitric oxide (NO) by oxidizing l-arginine. NO is a significant mediator in cellular signaling pathways. It serves as a crucial regulator in insulin secretion, vascular tone, peristalsis, angiogenesis, neural development and inflammation. Due to its important role, the inhibition of these vital enzymes provides therapeutic applications that target NOSs.

Prokaryotic proteins that are homologous to animal NOSs have been identified and characterized, both in terms of enzymology and biological function. In contrast to mNOSs, which possess both a catalytic and a reductase domain, the bacterial enzymes lack reductase domains and require the supply of suitable reductants to produce NO. A notable exception is a NOS from a gram-negative bacterium that contains a new type of reductase module.

Bacterial NOSs seem to have functions that differ from those of mNOSs, including nitration of different metabolites and protection against oxidative stress. Bacterial NOSs provide a better understanding of the mechanism of NO synthesis and unveil a variety of new functions for NO in microbes.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

A major problem with bacterial biofilms is the inability of the host immune system and/or antibiotics and other antimicrobials to gain access to the bacteria protected within the biofilm. Thus, in certain embodiments an agent is employed to break through the protective barrier of biofilms to treat or kill the associated bacterial infections as the biofilm can act as a reservoir for future acute infections often with lethal consequences. Although a laser can be used to kill bacteria, this method in isolation does not necessarily remove the bacteria, and thus a biofilm can remain on the implant which can hinder osseointegration and may act as a source of later infection. Antimicrobial agents are not effective at normal dosage, as the minimum inhibitory concentration for antibiotics for an organism in biofilm mode might be 1000-1500 times higher than for the same organism in the planktonic state.

Certain embodiments of the present invention are directed to a prophylactic method for treating dental caries comprising administering (preferably directly after a professional dental cleaning, and/or after an antibiotic application and rinse thereof) a composition comprising: probiotics selected from the group consisting DDS-1 strain of *Lactobacillus acidophilus*, *Lactobacillus bulgaricus*, *Lactobacillus johnsonii*, *Bifidobacterium bifidum* and *Enterococcus faecium* in a unit dosage amount ranging from 1000 to 3000 mg. Useful probiotic agents include (in addition to the numerous others referenced herein) *Bifidobacterium* sp. or *Lactobacillus* species or strains, e.g., *L. acidophilus*, *L. rhamnosus*, *L. plantarum*, *L. reuteri*, *L. paracasei* subsp. *paracasei*, or *L. casei* Shirota; *Lachnospira*, *Veillonella*, *Faecalibacterium* and *Rothia*, and *Prevotella*.

Due to the dynamics of growth and adherence, the bacterial populations in the oral cavity are constantly changing, even during the intervals between normal daily oral hygiene treatments. The various species within oral biofilms function as a coordinated community that uses intra- and interspecies communication. Development of the oral microbial community involves competition as well as cooperation among the 500 species that compose this community, including the following: *Actinobacillus actinomycetemcomitans*, *Actinomyces israelii*, *Actinomyces naeslundii*, *Capnocytophaga gingivalis*, *Capnocytophaga ochracea*, *Capnocytophaga sputigena*, *Eikenella corrodens*, *Eubacterium* spp., *Fusobacterium nucleatum*, *Haemophilus parainfluenzae*, *Porphyromonas gingivalis*, *Prevotella denticola*, *Prevotella intermedia*, *Prevotella loescheii*, *Propionibacterium acnes*, *Selenomonas flueggei*, *Streptococcus gordonii*, *Streptococcus mitis*, *Streptococcus oralis*, *Streptococcus sanguis*, *Treponema* spp., and *Veillonella atypica*. Although *F. nucleatum* is often considered a periodontal pathogen, it may instead contribute to maintaining homeostasis and improving host defense against true pathogens. Thus, in certain embodiments, the population of *F. nucleatum* is increased to achieve a more healthy oral microbiome that reduces the likelihood of dental carries. Several oral bacterial species are also amenable to genetic manipulation for molecular characterization of communication both among bacteria and between bacteria and the host. As described herein, various embodiments are directed to the modification of the oral microbiome to favor some bacterial species and not others in order to promote a more healthy oral microbiome, thus reducing oral diseases, including the formation of dental caries.

It has been shown in vivo that veillonellae are not capable of colonizing the tooth surface without streptococci as metabolic partners and that larger populations of veillonellae develop in coculture with streptococci that recognize them as a coaggregation partner than in coculture with streptococci with which they do not coaggregate. *Veillonella*, is commonly found in a person's mouth, mostly living on the tongue and saliva. In various embodiments, selected bacteria, such as *Veillonella*, is purposefully presented on an oral strip that adheres to the mucosal membrane of a person. Preferably the *Veillonella* is modified to reduce at least one virulence factor, related to its ability to co-aggregate with *S. mutans*, thus forming dental plaque.

Such modification of bacteria includes the employment of CRISPR systems to delete virulence factors from certain bacteria and forming a more healthy biofilm thereby, leading to the occurrence of less dental cavities than would otherwise be expected to occur. Another aspect of certain embodiments includes making synthetic CRISPR-containing RNAs that target genes of interest and using them with Cas enzymes. The specificity of CRISPR-Cas systems permits one to design methods to target a single bacterial species so that only essential genes from that one species is targeted and cut up. CRISPR-Cas systems are employed in various ways in the many embodiments of the present invention to retain the beneficial bacterial communities intact and to offer protection against undesired bacterial pathogens. Particular embodiments of the present invention are directed to the employment of four specific bacterial genera—*Lachnospira, Veillonella, Faecalibacterium* and *Rothia*, with none, some or all of these species modified to enable them to form more healthy biofilms and thus reduce the likelihood of dental caries.

Many embodiments rely upon the ability to deliver agents via mucosal adhesive strips, such as described, for example, in U.S. Pat. No. 8,701,671, which is fully incorporated herein by this reference. In such a manner, one objective is to accept the beneficial traits of the microbiome's interaction with the human immune system while avoiding the infectious aspects of bacterial, viral and helminth aspects of such exposure to a human being.

Periodontal diseases are polybacterially induced, multifactorial inflammatory processes of the tooth attachment apparatus and are the primary cause of tooth loss after the age of 35. It is believed that the ability of such disease to escape detection and the failure of many to regularly visit a dentist to diagnose such a disease, leads to the prevalence of Alzheimer's disease as we see today. The elderly often show neglect of oral hygiene which can stimulate recurrent chronic oral infection, which promotes inflammation and then leads to confusion and dementia. Interfering with inflammation is thus one objective of the present invention and in certain embodiments, it is beneficial to combine anti-inflammatory agents with antibacterials.

Dentilisin is involved in the degradation of membrane basement proteins (laminin, fibronectin, and collagen IV), serum proteins (fibrinogen, transferrin, IgG, and IgA), including protease inhibitors (.alpha.1-antitrypsin, antichymotrypsin, antithrombin, and antiplasmin), and bioactive peptides. Degradation of tight junction proteins by dentilisin seems to enable the penetration of epithelial cell layers by this oral spirochete. Saliva inhibits dentilisin, attenuating its virulence properties but conserving LL-37 activity. Thus one aspect of the present invention is directed to the use of LL-37 to kill *T. denticola*. The human host defense peptide LL-37 is preferably administered via the strips of the present invention, especially those having encapsulated pockets of the agent such that administration thereof can be achieved by the patient upon tongue pressure being applied to a frangible shell present as part of the strip. Deficiency in the human host defense peptide LL-37 has previously been correlated with severe periodontal disease.

Other aspects of the present invention are directed to the diagnosis of unhealthful conditions that relate to the microbiome of the individual. For example, compared to the gut microbiome, oral sampling of bacteria is easier and more acceptable and provides a diagnostic medium to assess the oral microbiome and its relationship with systemic diseases including pediatric autism, irritable bowel syndrome, pediatric appendicitis, etc. and can be employed as a predictor of present or future diseases. In addition to bacteria, embodiments of the present invention involve the modification of fungal and viral members of the oral microbial community in order to address oral health and disease. The use of oral microbiome to advance human health forms many aspects of the present invention and provides a way to both diagnose and treat many long felt but unsolved health problems.

In various embodiments, the invention may include a selected (one or more, and preferably a collection that forms a healthy biofilm) probiotic microorganism, an inhibitor of enzymes that are involved in the release of certain compounds, such as volatile sulfur compounds (VSC), and preferably a sugar, such as xylitol. In some embodiments, the probiotic microbe is selected from the group consisting of *Lactobacillus* sp., *Lactococcus* sp., *Bifidobacterium* sp., and *Streptococcus* sp. In some preferred embodiments the probiotic microorganism includes *Lactobacillus reuteri, Lactobacillus salivarius, Lactococcus lactis, Lactobacillus brevis, Lactobacillus rhamnosus, Lactobacillus acidophilus, Lactobacillus plantarum, Lactobacillus casei, Lactobacillus paracasei*, and/or *Lactobacillus curvatus*. In certain embodiments, the microorganisms include: *Bifidobacterium longum* and xylitol. These can be presented and offered in the form of a capsule or tablet, especially one that includes a prebiotic, such as a fiber, preferably inulin. Useful probiotic agents include (in addition to the numerous others referenced herein) *Bifidobacterium* sp. or *Lactobacillus* species or strains, e.g., *L. acidophilus, L. rhamnosus, L. plantarum, L. reuteri, L. paracasei* subsp. *paracasei*, or *L. casei* Shirota; *Lachnospira, Veillonella, Faecalibacterium* and *Rothia*, and *Prevotella*. In one preferred embodiment, *L. reuteri, L. salivarius* and *B. lactis* are combined, in addition to xylitol, and offered together in a tablet or capsule. In preferred embodiments, an individual's saliva is normalized to a pH range between 6.2-7.4 prior to administering the probiotic microorganisms.

In still other embodiments, a combination of microorganisms is employed to combat dental caries. Thus, in one such embodiment, at least two and preferably at least three of the following are included: *Lactobacillus slaivarius, Lactobacillus plantarum, Lactobacillus rhamnosus* and *Lactobacillus acidophilus; S. oralis* and *S. salivarius*. Other LAB that may be employed in various embodiments include the following: *Lactobacillus slaivarius* CICC 23174; *Lactobacillus plantarum* CGMCC 1.557, *Lactobacillus rhamnosus* ATCC 53103, and *Lactobacillus acidophilus* ATCC 4356. In other particular embodiments, the use of *S. oralis* and *S. salivarius* may be used in combination to inhibit growth of *S. pyogenes*, with speculation being that *S. salivarius* may achieve this feat via bacteriocin secretion. Epithelial cells are believed to be protected from infection by *S. pyogenes* when a biofilm containing *S. oralis* and *S. salivarius* is applied, with *S. pyogenes* unable to adhere to such tissue, thus the individual is protected from the adherence, internalization, and cytotoxic effects of a sore throat.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus, one aspect of the present invention relates to the employment of probiotics-induced oxytocin to reduce migraine symptoms, especially in the form of an oral adhesive strip as further described herein.

Therefore, certain embodiments of the present invention are directed to a method of reducing the likelihood of dental caries by providing to an individual in need thereof a buccal bioadhesive strip, with such strip having a first and second side and having a surface comprising a pattern defined by a plurality of spaced apart features each having at least one microscale dimension and having at least one neighboring feature having a substantially different geometry. Preferably the average spacing between adjacent ones of such features is between 0.5 and 5 .mu.m. FIG. 2(*a*)-(*d*) illustrate some exemplary surface architectural patterns according to the invention. A bioadhesive is employed that is adapted to bind to a mucosal membrane for at least 1 hour while inside an individual's mouth. Preferably the strip includes xylitol. In other embodiments, the strip includes an encapsulated feature containing a desired bacteria, preferably selected from the group consisting of *Lachnospira, Veillonella, Faecalibacterium* and *Rothia*. It is preferred to remove from the oral cavity of the individual gram negative bacteria associated with periodontitis, and within 2 hours thereof, to provide the individual with the strip. Still other embodiments include a strip that includes *Lactobacillus reuteri* bacteria to induce a sustained induction of oxytocin, and providing the individual with an amount of antibiotic sufficient to reduce the number of undesired bacteria in the oral cavity. Prior to the use of the strip, an antibiotic selected from the group consisting of tetracycline hydrochloride, doxycycline, and minocycline may be used to reduce the number of undesired bacteria in the oral cavity. One objective of several embodiments of the present invention is to retard the growth conditions for spirochetes and *P. gingivalis*. In still other embodiments, *Veillonella* and/or *Prevotella* bacteria is provided on the strip.

As one of skill in the art will appreciate, the strip may be made to include at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. Preferably, the strip includes at least 0.2% xylitol by weight. In certain embodiments, the strip comprises bioluminescent material. Preferably the strip is dissolvable in a person's mouth within a period of 1 hour. In certain preferred embodiments, the strip has least one encapsulated feature that contains an agent selected from the group consisting of an antibiotic; lactic acid bacteria; and xylitol, e.g. at least 200 mg of xylitol. Such a frangible capsule may be constructed so that it may be broken by the individual pressing against said strip with the individual's tongue.

Certain embodiments of the present invention relate to particular combinations of functional ingredients, namely zinc-based compounds (e.g. zinc acetate, chloride, citrate, sulphate) with a topically administered oral probiotic (e.g. *L. brevis* CD2, *Streptococcus sanguinis* BCC23, *Lactobacillus acidophilus, Lactobacillus bulgaricus, Lactobacillus johnsonii, Bifidobacterium bifidum Enterococcus faecium, Bifidobacterium* sp. or *Lactobacillus* species or strains, e.g., *L. acidophilus, L. rhamnosus, L. plantarum, L. reuteri, L. paracasei* subsp. *paracasei*, or *L. casei* Shirota, including *Lachnospira, Veillonella, Faecalibacterium* and *Rothia*, and *Prevotella*) and at least one bioactive flavonoid (e.g. baicalein, naringenin, catechins, the product maritime pine bark extracts sold under the trademark Pycnoqenol™, quercetin, trans-resveratrol, Luteolin, kaempferol, hesperidin, hesperetin, naringin, diosmin, rutin, nobiletin, and tangeretin.) The present inventors have appreciated that certain zinc-based compounds included in formulations as set forth herein re useful for a variety of purposes, including anti-malodor formulations used in the oral cavity to promote an inhibitory effect on oral microbes that generate substances of a malodor, and thus cause halitosis.

While not bound by theory, it is believed that two general mechanisms can be employed to achieve a reduction in halitosis: creation of conditions in the oral cavity such that direct binding with gaseous H2S is accomplished, and/or the suppression of the growth of Volatile sulfur compound (VSC)-producing oral bacteria. Volatile sulfur compounds (VSC), such as methylmercaptan and hydrogen sulfite, are produced by bacteria. Such bacteria are able to colonize the lingual dorsum and are implicated in the generation of halitosis. *Porphyromonas, Prevotella, Actinobacillus*, and *Fusobacterium* bacterial species are some of the major bacteria that produce VSC's and such bacteria are found in the oral cavity of individuals in areas that are not distal to the tonsils.

In various embodiments, zinc salts, in combination with other components of formulations as described herein, are used as an anti-plaque and anti-calculus agent in oral products. It is believed that zinc binds in vivo to plaque and calculus, and thereby inhibits nucleation and crystal growth of calcium phosphates. Application of formulations that include zinc salts include mouthwashes and other dentifrice applications.

As another component of formulations of certain embodiments, oral probiotics are employed for various purposes, one of which is to competitively compete with existing bacteria, and in particular pathogenic bacteria, present in an individual's oral cavity. Certain probiotics act to lower the pH to be within a physiologic range, thus disrupting pathogenic biofilms and/or producing post-biotic compounds beneficial to an individual's oral health, often increasing the alpha diversity of an individual's oral cavity.

Yet another component of preferred embodiments of the present invention include bioactive flavonoids that provide a multitude of actions in the oral cavity, including prebiotic feeding of beneficial bacteria, acting as a microbial substrate for production of additional health-promoting post-biotics, antimicrobial action of eliminating pathogenic bacteria and other undesired microorganisms, disrupting pathogenic biofilms, and anti-inflammatory and epithelial barrier strengthening actions in the buccal and gingival tissues.

Various modes of administration of particular formulations of the present invention involve application to the oral cavity via toothpaste, mouth washes, gargle solutions, nose sprays, mouth sprays, throat sprays, chewing gum, hydrogel, oral strips, and creams, etc. When orally administered the formulations of the present invention deliver a synergistic and multifunctional approach to alleviate, disrupt, and/or prevent a variety of conditions and/or diseases, including halitosis; plaque deposition; gingivitis; periodontitis and oral biofilm formation by pathogenic bacteria.

Other embodiments of the invention that are directed to companion pets include the administration of desired bacterial compounds, etc, via including the same in an extruded chew, jerky chew, or other methods of delivering active components in a manner that requires mastication and shearing mechanical forces and that further aid in plaque removal.

Many bacterial species connected to oral disease, such as periodontitis and dental abscesses, can produce significant amounts of VOCs. Compounds such as butyric and propionic acid have been found in increased amounts from the gingival crevicular fluid and plaque of patients with chronic periodontitis. Bacterial volatile compounds have potential as biomarkers for oral infections, especially because they can be measured non-invasively from the exhaled breath or the salivary headspace. It is believed that morning breath contains the highest amounts of VOCs due to their accumulation and the undisturbed bacterial activity during a night's sleep. Changes in the oral pH affect the solubility of certain VOCs. Some compounds connected specifically to the subgingival anaerobes from the *Treponema, Porphyromonas*, Tannerella, and *Prevotella* genera, which increase in periodontitis compared to a healthy mouth, include methanol, pentanal, 3-penten-2-one, 1,3-pentadiene, methyl methacrylate, 3-methylbutyl propanoate, and 2-methyl-1-propanethiol.

Supragingival bacteria with cariogenic properties from *Streptococcus, Lactobacillus* and *Propionibacterium* genera are believed to be connected to cyclohexanone, 2-pentanone, octanal, and DMS. Salivary bacteria produce especially short- to medium-chain fatty acids, as well as some ketones. S-methyl pentanethioate is the only VSCs connected in vitro to salivary bacteria.

Even though halitosis is a separate condition from such oral infectious diseases as periodontitis, there is a significant correlation between malodor and the increased number of periodontal pathogens on the tongue surface, increased number and depth of periodontal pockets, and increased oral bone loss and bleeding. Oral diseases increase the production of odorous bVOCs in breath and these bVOCs are important in relation to halitosis and vice versa. Thus, many of the compounds from different oral bacteria are also markers for halitosis.

The malodorous "morning breath" compounds include sulfur compounds, such as methanethiol, hydrogen sulfide, DMS, and 2-methyl-1-propanethiol, as well as acetic, butyric and valeric acid, acetaldehyde, octanal, phenol, methyl methacrylate, indole, ammonia, and isoprene. The present inventors submit that most of the odorous VOCs found in a person's morning breath are of bacterial origin and thus, aspects of the present invention are directed to reducing the causes of such bacterial production of VOCs.

While certain embodiments of the present invention are described herein in the context of use for humans, it should be understood that still other applications of certain embodiments are for the treatment of oral cavities of other animals, including mammals, and especially companion animals, such as canines and felines.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications.

BRIEF DESCRIPTION OF THE FIGURES

FIG. 4 is an illustration of a pre-made sheet of strips that can be disassociated with the sheet and then applied to mucosal or dental membranes.

FIG. 5 is a side view of one embodiment of a strip having an outer layer, an adhesive layer, a layer with an encapsulated agent contained there between.

FIG. 6 is a side view of one embodiment where the encapsulated agent is encapsulated into small beads that are frangible via pressure of an individual's tongue.

DETAILED DESCRIPTION OF VARIOUS EMBODIMENTS OF THE INVENTION

Figure 1:
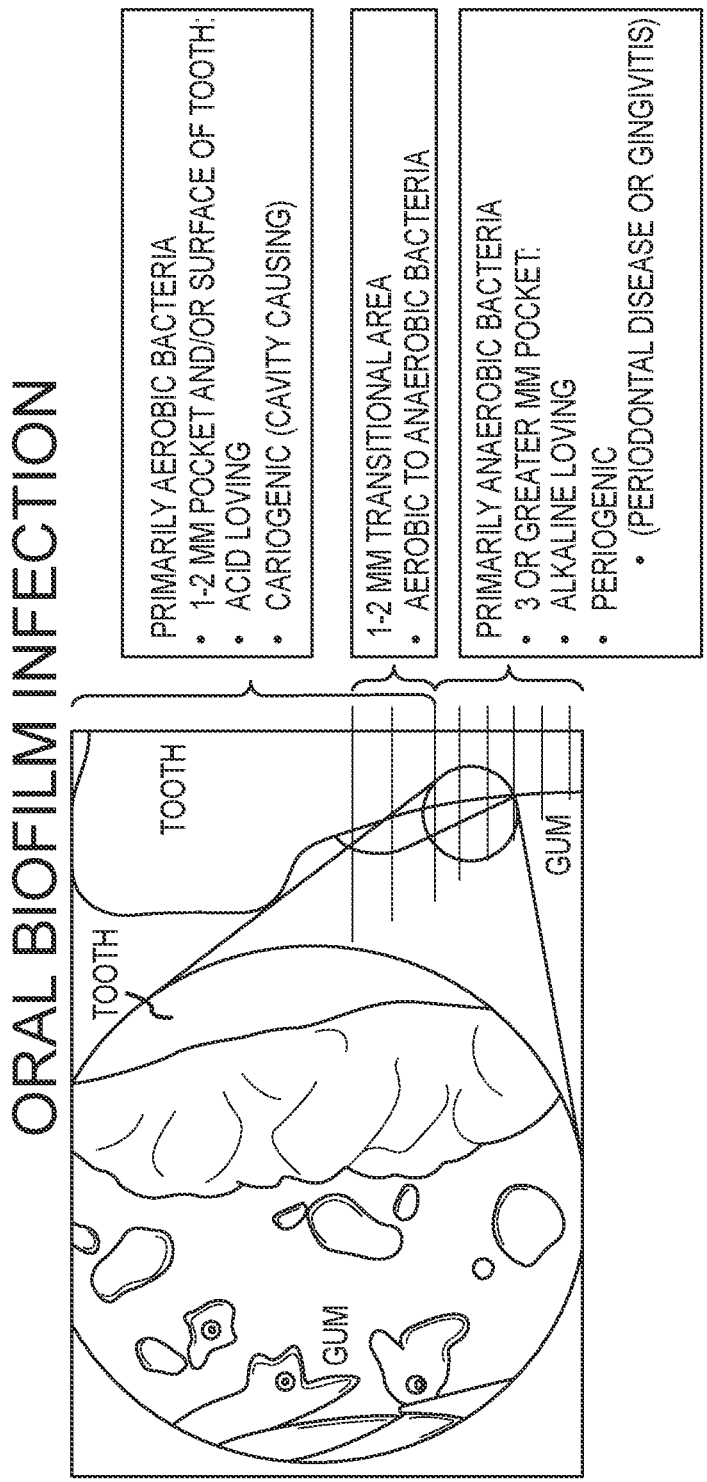
FIG. 1 is an illustration of oral biofilm infections of the human body, showing a human tooth, gum and sites of periodontal disease.
Figure 2A:
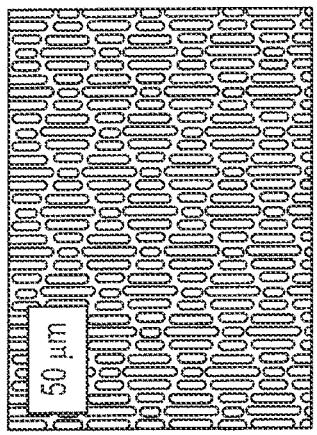
FIG. 2(a)-(d) illustrate some exemplary surface architectural patterns according to one aspect of certain embodiments of the invention.
Figure 2B:
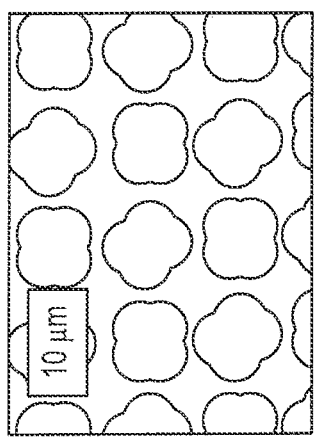
Figure 2C:
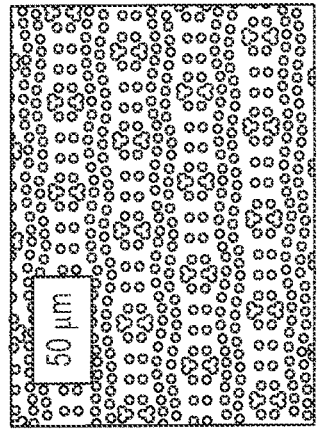
Figure 2D:
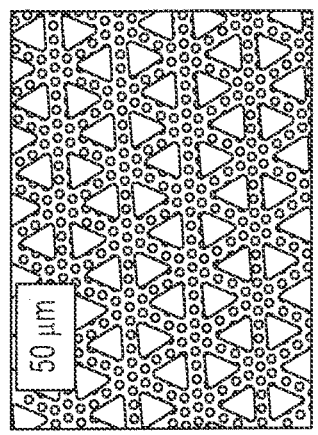
Figure 3:
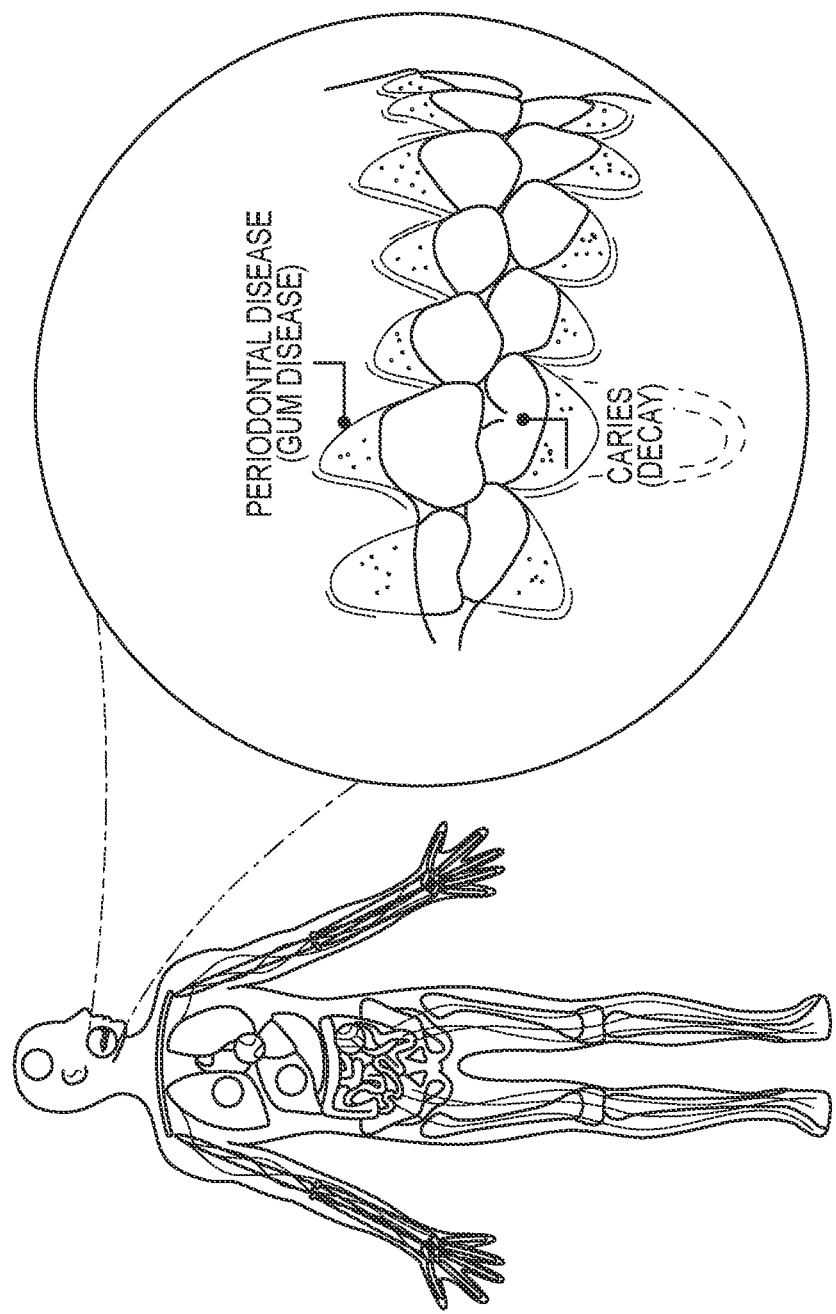
FIG. 3 illustrates a site of periodontal disease and to areas of the human body believed to be causally affected by inflammation and bacterial infections stemming therefrom.

Dental plaque, a sticky colorless film, is caused by bacterial deposits accumulating on tooth or implant surfaces along the gingival margins and results in the destruction of tooth-supporting tissues. Dental plaque formation starts in cracks, grooves and surface roughness on teeth and/or dental implants. In any given plaque sample, it is not uncommon to detect 30 or more bacterial species. Biofilms that colonizes the tooth surface may be among the most complex biofilms that exist in nature. The bacteria associated with periodontal diseases reside in biofilms both above and below the gingival margin. The supragingival biofilm is attached to the tooth or the implant and predominated by *Actinomyces* species. The subgingival biofilm is typically more complex and can either attach to the tooth or implant, or to the gingival tissue. Three microbe species are believed to be main players in the cause the periodontal diseases: *A. actinomycetemcomitans, P. gingivalis* and *B. forsythus*. Also, *F. nucleatum, Campylobacter rectus, P. Intermedia, P. nigrescens, Eubacterium nodatum, P. micros* and various spirochetes have been singled out that may also be important species in periodontal disease.

The destruction of tooth-supporting tissues results in a deepening of the space (periodontal pocket) between the root of the tooth and the gum tissue. Second to tooth decay, periodontal diseases are the most frequent oral diseases and may lead to partial or complete tooth or bone loss. It has been estimated that they affect as much as between 70-90% of the world population, and they are the major cause of tooth loss in people over 35 years of age. In periodontitis the infection has progressed to involve the oral tissues which retain the teeth in the jawbone. If untreated, periodontitis ultimately leads to loss of the affected tooth. Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase, finally causing spontaneous loss of a tooth or a necessity of tooth extraction. Treatment of periodontal diseases usually involves the removal of bacterial deposits and dental calculus. However, it is difficult to have full access for treating deeper periodontal pockets, resulting in remaining bacteria that may re-infect the tissue.

Nitric oxide (NO) is a free radical with a gas structure that is created from an extensive diversity of cells and tissues. and can be diffused easily from the membranes. It is involved in numerous physiological activities, such as cell death, immune regulation, neurotransmission, and vascular relaxation and is detected in oral cavity tissue. Although other free radicals are harmful to cells at every concentration, NO at low concentrations has a role in important physiologic functions. High concentrations of NO in the gastric lumen, leads gastric relaxation and causes relief of functional dyspepsia symptoms, while it also has a crucial role in protecting the stomach from hazardous pathogens. The oral flora form the most complex microbial community of the human body, and consist of more than 700 types of bacteria, viruses, and fungi. Saliva plays a crucial role in the host defense mechanism by including several specific and nonspecific defense factors. Nitrate within saliva is rapidly converted into NO by oral flora and salivary peroxidase, protecting the oral cavity and stomach from pathogenic microorganisms via the gastrointestinal—salivary cycle of NO and its metabolites. A relationship has been demonstrated between increased salivary NO levels and several oral diseases, particularly dental caries. Thus, one aspect of the present invention is directed to modification of the levels of NO in the oral cavity to reduce the likelihood of dental caries. Dental caries occur through a complex interaction of many factors, but the regulation of NO levels in the oral cavity is one aspect of the present invention.

$O_2$ and NO act as environmental cues that trigger the coordinated expression of virulence genes and metabolic adaptations necessary for survival within a host. NO concentrations may be produced by fecal microbiota from nitrate, with the nitrate being reduced to ammonium by the dissimilatory nitrate reduction to ammonium (DNRA) pathway. Gastrointestinal microbiota can generate substantial amounts of NO by DNRA, rather than by the generally accepted denitrification or L-arginine pathway. Bacterial nitrate reduction to ammonia, as wen as the related NO formation in the gut, is believed to be an important aspect of the overall mammalian nitrate/nitrite/NO metabolism, demonstrating how the microbiome links diet and health.

Biofilm initiated diseases are by no means unique to the oral cavity. Approximately 65% of infections that affect the human are caused by organisms growing in biofilms. These include dental caries, periodontal disease, otitis media, musculoskeletal infections, necrotizing fasciitis, biliary tract infection, osteomyelitis, bacterial prostatitis, native valve endocarditis, meloidosis, prosthetic as well as orthopedic complications and cystic fibrosis pneumonia. Characteristics are persistence and chronicity of the infections as well as the difficulty in eradication.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. Other embodiments, more focused on the reduction in the likelihood of getting dental caries, are focused on *S. mutans* and *Veilonella*, as those two bacteria combine to form dental plaques. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

Streptococci constitute 60 to 90% of the bacteria that colonize the teeth in the first 4 hours after professional cleaning. Other early colonizers include *Actinomyces* spp., *Capnocytophaga* spp., *Eikenella* spp., *Haemophilus* spp., *Prevotella* spp., *Propionibacterium* spp., and *Veillonella* spp.

Antibiotics can be prescribed at a low dose for longer term use, or as a short-term medication to deter bacteria from re-colonizing. Preferably, in various embodiments of the present invention, strips that contain appropriate amounts and types of antibiotics are employed to adjust the population of the oral and the gut microbiome of a person to alleviate migraine and dizziness symptoms. Incorporated by reference in its entirety is U.S. Pat. No. 9,445,936, directed to the use of mucosal strips, and especially oral strips, that can be provided with various bacterial components to adjust and modify the oral microbiome of an individual. It is sometimes advisable to undergo a treatment with antibiotics so as to reduce the number of other undesired bacteria in the oral cavity, prior to the use of the strips having the desired bacteria included thereon. Antibiotics which include tetracycline hydrochloride, doxycycline, and minocycline are the primary drugs used in periodontal treatment and that are preferred for use in the strips as described herein. Such strips with these agents have antibacterial properties, reduce inflammation and block collagenase (a protein which destroys the connective tissue). Metronidazole is generally used in combination with amoxicillin or tetracycline to combat inflammation and bacterial growth in severe or chronic periodontitis and the use of these antibiotics on or encapsulated on strips of the present invention permit selective administration to the oral cavity in a manner that has never been done before. In preferred embodiments, the direct delivery of antibiotics to the surfaces of the gums by using the strips as described herein is preferred and are extremely effective when used after scaling and root planing procedures. Among the various existing agents that can be incorporated into the strips of the present invention, especially those that encapsulate such agents such that a person can self-administer the agents via tongue pressure applied to frangible shells containing such material, are as follows: a doxycycline gel that conforms to the contours of gum surfaces and solidifies over them; Chlorhexidine, a powerful antibacterial antiseptic; tetracycline hydrochloride; metronidazole; and Minocycline.

Probiotics are living microorganisms that have beneficial effects on the health of the host. The most used probiotics are lactobacilli and bifidobacteria. Effects of probiotics are dependent on the used species and strain. Certain methods of the present invention are directed to probiotic formulations included on or encapsulated into a strip of the present invention such that the desired bacteria is delivered to the oral cavity, either directly to dental surfaces and in other embodiments to mucosal membranes. Such strips may include one or more desired bacterial species, useful for promoting or maintaining the health and general well-being of humans, including but not limited to the following: a combination of different probiotics (*Lactobacillus acidophilus, Lactobacillus bulgaricus, Enterococcus faecium, L. salivarius*, and *Bifidobacterium bifidum*, etc.) can be employed for such purpose; *Enterococcus faecium*, including strain NCIMB 40371, etc.

In certain embodiments, the strips as described herein are employed to modify the oral microbiome of an individual to reduce the likelihood of dental caries. Thus, a buccal bioadhesive strip is preferably used that has a first and second side, with the first side having a surface comprising a pattern defined by a plurality of spaced apart features each having at least one microscale dimension and having at least one neighboring feature having a substantially different geometry, and wherein an average spacing between adjacent ones of said features is between 0.5 and 5 .mu.m in at least a portion of the surface. The first side has a bioadhesive that is adapted to bind to a mucosal membrane for at least 1 hour while inside a person's mouth. The strip may, for example, extend over a majority of the soft palate and preferably includes xylitol. Other embodiments have the strip including at least one encapsulated pocket containing one of an analgesic, a lactic acid bacteria, or another of the desired bacteria as described herein. FIG. 4 is an illustration of a pre-made sheet 100 of strips 120 that can be disassociated with the sheet and then applied to a dental surface or mucosal membrane. FIG. 5 is a side view of one embodiment of a strip 120 having an outer layer, an adhesive layer, a layer with an encapsulated agent contained there between. FIG. 6 is a side view of one embodiment where the encapsulated agent 110 is encapsulated into small beads that are frangible via pressure of an individual's tongue pressing against the strip.

A major problem with bacterial biofilms is the inability of the host immune system and/or antibiotics and other antimicrobials to gain access to the bacteria protected within the biofilm. Thus, a need exists to break through the protective barrier of biofilms to treat or kill the associated bacterial infections as the biofilm can act as a reservoir for future acute infections often with lethal consequences. Although a laser can be used to kill bacteria, this method in isolation does not necessarily remove the bacteria, and thus a biofilm can remain on the implant which can hinder osseointegration and may act as a source of later infection. Antimicrobial agents are not effective at normal dosage, as the minimum inhibitory concentration for antibiotics for an organism in biofilm mode might be 1000-1500 times higher than for the same organism in the planktonic state. Periodontal diseases are infections caused by microorganisms that colonize the tooth or implant surface at or below the gingival margin. While these infections have many properties in common with other infectious diseases, they exhibit unique properties conferred by their site of colonization and the nature of the environment in which they reside. The onset of the diseases is usually delayed for prolonged periods of time after initial colonization by the pathogens.

Thus certain embodiments of the present invention are directed to a prophylactic method for treating an individual to reduce the likelihood of dental caries comprising (after the above referenced steps of removing pathogenic bacteria associated with a person's periodontitis, including after antibiotic applications) administering on a daily basis to humans a composition comprising: probiotics selected from the group consisting DDS-1 strain of *Lactobacillus acidophilus, Lactobacillus bulgaricus, Lactobacillus johnsonii, Bifidobacterium bifidum* and *Enterococcus faecium* in a unit dosage amount ranging from 1000 to 3000 mg. Useful probiotic agents include (in addition to the numerous others referenced herein) *Bifidobacterium* sp. or *Lactobacillus* species or strains, e.g., *L. acidophilus, L. rhamnosus, L. plantarum, L. reuteri, L. paracasei* subsp. *paracasei*, or *L. casei* Shirota; *Lachnospira, Veillonella, Faecalibacterium* and *Rothia*, and *Prevotella*.

Human oral bacteria interact with their environment by attaching to surfaces and establishing mixed-species communities. Several oral bacterial species are amenable to genetic manipulation for molecular characterization of communication both among bacteria and between bacteria and the host. Due to the dynamics of growth and adherence, the bacterial populations in the oral cavity are constantly changing, even during the intervals between normal daily oral hygiene treatments. The various species within oral biofilms function as a coordinated community that uses intra- and interspecies communication.

Development of the oral microbial community involves competition as well as cooperation among the 500 species that compose this community, including the following: *Actinobacillus actinomycetemcomitans, Actinomyces israelii, Actinomyces naeslundii, Capnocytophaga gingivalis, Capnocytophaga ochracea, Capnocytophaga sputigena, Eikenella corrodens, Eubacterium* spp., *Fusobacterium nucleatum, Haemophilus parainfluenzae, Porphyromonas gingivalis, Prevotella denticola, Prevotella intermedia, Prevotella loescheii, Propionibacterium acnes, Selenomonas flueggei, Streptococcus gordonii, Streptococcus mitis, Streptococcus oralis, Streptococcus sanguis, Treponema* spp., and *Veillonella atypica*. Although *F. nucleatum* is often considered a periodontal pathogen, it may instead contribute to maintaining homeostasis and improving host defense against true pathogens. One aspect of several embodiments of the present invention are directed to modification of bacteria to affect the association with other bacteria, such as the ability to coaggregate to form dental plaque, etc, To make such modifications, CRISPR systems may be employed to modify, e.g., delete or weaken certain virulence factors of one or more bacteria as set forth herein.

Competitive and cooperative mechanisms may be central to successful mixed species colonization as well as the proper succession of genera known to occur on teeth in both health and disease. Within the oral cavity, bacteria form multispecies communities that are distinguishable primarily by their location (supragingival versus subgingival versus epithelial). The subgingival community has the highest species richness and the greatest capacity for pathogenic outcome, such as periodontal tissue destruction. It has been shown in vivo that veillonellae are not capable of colonizing the tooth surface without streptococci as metabolic partners and that larger populations of veillonellae develop in coculture with streptococci that recognize them as a coaggregation partner than in coculture with streptococci with which they do not coaggregate.

While migraines and Alzheimer's Disease share certain similarities in terms of bacterial and nerve passages of material to the brain, it is as yet unknown if the spirochetes believed responsible for the majority of AD is also associated with migraines and cluster headaches. About 60 oral species of *Treponema* have been identified, and spirochetes constitute a large percentage of the total oral bacterial numbers. Accordingly, a large *T. denticola* population could benefit greatly through interaction with a small *P. gingivalis* population. A stimulatory effect of *P. gingivalis* supernatant on *T. denticola* growth points to a synergistic interaction between *P. gingivalis* and other anaerobic bacteria such as oral spirochetes, and may be increased growth and increased virulence of these potential periodontal pathogens.

Caries can be divided into the following three types according to the location of occurrence: crown caries, root caries and mixed-type caries affecting both the crown and root. The relationship between dental caries and periodontal disease remains controversial, however, caries of both the crown and root have been positively correlated with periodontitis and caries on the root of teeth have been positively correlated with periodontitis in the elderly. Thus, aspects of the present invention are directed to the treatment of not just caries, but of associated periodontitis.

One aspect of the present invention is to avoid a large population of spirochetes in the oral cavity and one way of doing so involves limiting the population of other bacteria that spirochetes depend upon to thrive and grow. Thus, one aspect of the present invention is directed to the limitation or destruction or the retarding of growth conditions for spirochetes, which includes the limitation of the presence of *P. gingivalis*. Subtle regulation of gene expression in any organism within a community may lead to significant changes in the organism's ability to participate in community activities, such as use of community-formed metabolic end products as nutrients. Thus, interference with the biofilms relied upon for spirochetes growth and maintenance is one aspect of the present invention, which may be achieved via the use of oral strips of the present invention that have structural features thereon that deter bacteria growth, and that may also have antibiotics as well as beneficial bacteria residing thereon, and alternatively or in addition to, may have xylitol on the strip.

One aspect of the present invention is to trigger small changes in a person's oral and/or gut microbiome such that they cause large shifts in population composition and metabolic output of mixed-species communities. In certain embodiments, this is accomplished by inactivation of a gene (via CRISPR-Cas or CRISPR-Cpf1) involved in mixed-species community formation to cause a subtle variation in an organism's phenotype only during critical transitions in population composition and have no effect on population composition before or after the transition.

In still further particular embodiments, the *Treponema denticola* genome is modified to target the expression of particular chromosomal integrons, as it is the only human-associated bacterial species that harbors chromosomal integrons, with no integrons in other *Treponema* species being found. For example, in one particular embodiment of the present invention, genes from *Treponema* are modified to excise one or more virulence factors to address the progression of diseases, such as the buildup of dental plaque, gingivitis, periodontitis, Alzheimer's disease, dizziness, migraines and cluster headaches, by addressing the causative factors of such diseases in the oral cavity of the person, prior to the full-blown development of such diseases. Chronic periodontitis is an inflammatory disease that is caused by the accumulation of bacteria in the form of a biofilm in the periodontal pocket. It can be treated with oral hygiene in conjunction with β-lactam antibiotics. Many oral anaerobic bacteria associated with chronic periodontal diseases have developed resistance to β-lactam antibiotics by virtue of their production of β-lactamase enzymes. Using CRISPR-Cas techniques to delete virulence factors and to restore antibiotic sensitivity to permit use of known effective antibiotics, is one aspect of the present invention.

A high prevalence of β-lactamase-producing oral anaerobic bacteria has been found in patients with chronic periodontitis. As a large percentage of bacteria carry a gene that renders them resistant to β-lactam antibiotics, alternative antimicrobial agents should be employed in patients that are non-responsive to β-lactam antibiotics. Use of CRISPR-Cas systems to render particular bacteria susceptible to such antibiotics is one aspect of the present invention, as well as the purposeful exposure of a person's oral cavity (after existing bacterial flora has been substantially removed) to replace the flora with a CRISPR-Cas system modified bacteria culture such that the control over the oral population of bacteria can be achieved, such as by rendering such bacteria susceptible to antibiotics.

Yet another aspect of the present invention is directed to the employment of phospholipid vesicles in addressing desired modifications to the human microbiome, and in particular to the oral microbiome. Bacterial membrane vesicles (MVs), released by many bacteria, mainly consist of the cell membrane and typically range from 20 to 400 nm in size. Bacterial MVs are involved in several biological functions, such as delivery of cargo, virulence and gene transfer. Although MV biogenesis and biological roles are yet to be fully understood, one aspect of the present invention relates to the genetic engineering of such MVs to tailor them for applications in drug delivery systems and nanobiocatalysts, MV vaccines, etc. MVs have been found to mediate diverse functions, including promoting pathogenesis, enabling bacterial survival during stress conditions and regulating microbial interactions within bacterial communities, Modification and increased expression of such vesicles, including the ability to employ CRISPR-Cas systems to affect the transfer of desired components to the oral cavity via such vesicles, is part of various embodiments of the present invention. The existence of membrane vesicles increases the complexity involved in the diffusion of secreted substances during microbial interactions and MV secretion has been observed in Gram-negative bacteria as well as in other prokaryotes, including Gram-positive bacteria and archaea. MVs contain proteins, DNA, RNA and quorum sensing signals, and these substances are transferred to cells. MVs have unique characteristics, including the fact that several chemical substances are highly concentrated in MVs, the interior substances in MVs are protected against environmental stresses, and MVs play a role in effectively delivering these substances to cells.

In one particular aspect of the present invention, MVs of human specific pathogens are employed to incapacitate the pathogenic nature of such bacteria. The association between MVs and eukaryotic cells has been studied in pathogenic bacteria, and MVs secreted from pathogens transfer virulent factors to cells. In particular, specific proteins localized on the surface of MVs increase the association with epithelial cells, believed to be due to increasing the association of MV lipopolysaccharide with cells.

Microbial predation using MVs occurs when virulent factors or peptidoglycan hydrolytic enzymes contained in MVs are transferred to other bacterial cells. It has been suggested that the mechanism of bacterial lysis via MVs secreted from Gram-negative bacteria differs in whether recipient cells are Gram-negative or positive. Thus, cell-to-cell communications in the oral cavity involve microbes intricately communicating through methods using MVs, thereby influencing interspecies networks, microbial community organization and ecosystem dynamics. Employment of the specially surfaced structured strips of the present invention may be used to alter the population of an individual's microbiome in a manner that can deter the progression of bacterial related diseases, such as the formation of dental caries, and also including a build up of dental plaque, halitosis, gingivitis, periodontitis, migraines, cluster headaches and Alzheimer's. With respect to treatment, several embodiments employ Graphene oxide nanosheets, and especially in the form of the strips as described herein, to deliver an effective antibacterial material against dental pathogens, including especially *Treponema denticola*.

One aspect of certain embodiments of the present invention relate to a series of steps to be undertaken to address the killing and elimination of certain gram negative bacteria that are associated with periodontitis, followed by the purposeful application of a composition having beneficial bacteria that are adapted to growth so as to populate a person's mouth and thus prevent the reestablishment of harmful bacteria that could, if permitted to persist in a person's mouth, lead to various maladies, including a build up of dental plaque, halitosis, gingivitis, periodontitis, Alzheimer's disease, cluster headaches and migraines. In particular embodiments, strips are employed that have at least one encapsulated drug containing capsule that when broken or fractured, can release a predetermined amount of a drug, such as one effective to reduce if not eliminate certain gram negative bacteria and/or spirochetes that are believed responsible for periodontal disease, and in one preferred embodiment involves the use of metronidazole, preferably encapsulated or imbued onto a bioadhesive strip of the present invention. Certain embodiments of the present invention employ oral pharmaceutical compositions that include metronidazole, especially contained within a release layer of a bioadhesive strip that dissolves or erodes in the oral cavity.

Thus, in certain embodiments, the present invention provides an ability of a patient to purposefully cause the rupture of an encapsulated packet or pocket (e.g. a space in a strip that captures the agent of choice, which is released upon the rupture of such packet/pocket) that is associated with a strip that is adapted to be placed in association with a person's gums or dental surfaces, with the encapsulated material preferably being an antibiotic, e.g. metronidazole, etc., adapted to kill gram negative bacteria, and especially microbes associated as a causative agent in periodontitis or the build up of dental plaque.

Metronidazole is a nitroimidazole antibiotic with antibacterial activity against obligate anaerobic bacteria and certain protozoan parasites. The usual oral antibacterial therapies for treating pathologies have often given contradictory results. For instance, excessive dilution of the active ingredient has been observed in the intestinal lumen. This dilution is believed to be due to the premature release of the antibacterial agent from the pharmaceutical form even before reaching the duodenum such as in the stomach and in the immediate vicinity of the patient's pyloric valve. Similarly, in the oral cavity, use of metronidazole in a systemic fashion has limited results, as it does not persist in a concentrated enough form to kill undesired microbes that are entrenched in the gum regions of a person's mouth. Thus, in various embodiments of the present invention, metronidazole (or other suitable antimicrobials) is provided in adhesive strips that are configured for providing the oral cavity and/or dental surfaces with a sufficiently high level and dosage of the drug to accomplish the desired killing of certain bacterial species, including particular spirochetes such as *T. denticola*, but also including other bacteria, such as *P. gingivalis*, and/or *S. mutans* and/or *Veilonella*.

In another particular aspect, a genetically modified microbe, such as a bacteria of the species *T. denticola* and/or *Prevotella* and/or *S. mutans* and/or *Veilonella*, includes an inducible promoter directing expression of an essential protein and/or is modified such that expression of virulence factors are substantially reduced or eliminated. In certain embodiments, a composition comprises one or more genetically modified microbes, such as a bacteria of the species *T. denticola* and/or *Prevotella* and/or *S. mutans* and/or *Veilonella*, each of which are genetically modified, and especially by employment of CRISPR-Cas or Cpf1 systems to attenuate virulence factors, etc. CRISPR-Cas or Cpf1 modified microbes in which expression of an endogenous pathogenic protein is substantially reduced or eliminated in the one or more genetically modified bacteria include an inducible promoter regulating the expression of a virulence factor for such microbe.

Still other embodiments are directed to the use of bacteriophages modified to attack particular bacteria, especially *T. denticola* and/or *Prevotella*, and/or *S. mutans* and/or *Veilonella* to reduce the populations of one or the other in the oral cavity. In accordance with the present invention, native bacterial adaptive immune systems can be modified to thwart the conventional ability to confer immunity against bacteriophage infection. The CRISPR-Cas sequences, which are present in approximately 40% of eubacterial genomes and nearly all archaeal genomes sequenced to date, is employed to reverse the resistance to various antimicrobial agents such as small molecule antibiotics and bacteriophages.

Thus in certain embodiments, the innovative method is directed to decreasing the relative representation of a specific strain of bacteria, preferably *T. denticola* and/or *Prevotella*, and/or *S. mutans* and/or *Veilonella* within a heterogenous population of oral bacteria, comprising contacting the heterogenous population of oral bacteria with a bacteriophage comprising a polynucleotide that expresses (a) an RNA-directed DNA-binding polypeptide comprising a nuclease module; and (b) a targeting module comprising a guide RNA, wherein the targeting module tethers the RNA-directed DNA-binding polypeptide to a target DNA sequence within, thereby producing a double-strand break within the target sequence, wherein the target sequence is unique to the specific strain of *T. denticola* and/or *Prevotella* and/or *S. mutans* and/or *Veilonella* bacteria.

In certain embodiments of the present invention, delivery of beneficial bacteria, after the removal of pathogenic bacteria and also after use of the strip treatments as described herein (e.g. including the administration of local antibiotics to oral tissues), is achieved in a manner that comports with where such bacteria are normally located in a person's body. For example, many of the bacteria that confer protection against autoimmune diseases and that are otherwise believed to promote health in humans, and as described herein, are normally resident in the human mouth. For instance, one of the FLVR bacteria recently touted as being beneficial in the prevention of disease, namely *Veillonella*, is commonly found in a person's mouth, mostly living on the tongue and saliva. In various embodiments, selected bacteria, such as *Veillonella*, is purposefully presented on an oral strip that adheres to the mucosal membrane of a person.

*Veillonella* is a small cocci bacterium that is anaerobic and needs carbon dioxide to grow. Although there are around 200 types of bacteria that grow in the oral cavity, *Veillonella* and *Streptococcus* bacteria work together in the early formation of dental plaque. As these two bacteria colonize and grow, they lay a matrix that supports the growth of other varieties of bacteria that live in plaque. *Veillonella* is found in the gut of humans and dental plaque. While considered non-pathogenic, it has been linked with rare cases of meningitis, osteomyelitis, and periodontal disease. It cannot metabolize carbohydrates, but instead uses organic acids like lactate. *Veillonella* plays a significant role in the formation of biofilms. It is able to coaggregate with other organisms, namely *Streptococcus mutans*, to form dental plaque as the two organisms have a mutualistic relationship with each other. *Veillonella* cannot adhere to the surface of teeth by itself, and so attaches to *S. mutans*. *Veillonella* can use the lactate product formed by *S. mutans* for its metabolism, in the process forming a less corrosive acid. One aspect of the present invention is directed to interfering with the co-aggregation of these two microorganisms, such as by modification of virulence factors of each or both bacteria to affect the resistance of a resulting biofiom to antimicrobial treatments.

In various embodiments of the present invention, bacterial species to be exposed to a person's oral (or in other embodiments, gut) microbiome, include those specifically modified by employing the CRISPR-Cas and CRISPR-Cpf1 systems to render the virulence factors of various bacteria ineffective. CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. In certain preferred embodiments, rather than using CRISPR-Cas, one employs the CRISPR-associated endonuclease Cpf1. e.g. a CRISPR from *Prevotella* and

*Francisella* 1 (Cpf1) nuclease for CRISPR-based genome editing, and incorporating 20150252358 to Maeder by this reference).

CRISPR-Cpf1 is a class II CRISPR effector that is distinct from Cas9, and is a single RNA-guided endonuclease that uses T-rich PAMs and generates staggered DNA double stranded breaks instead of blunt ends. Its smaller protein size and single RNA guide requirement makes CRISPR applications simpler and with more precise control. The human gut is a rich habitat populated by numerous microorganisms, each having a CRISPR system. To comply with written description and enablement requirements, incorporated herein by the following references are the following patent publications: 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; 2014/0255351 to Berstad et al.; 2015/0086581 to Li; 2016/0311913 to Sun; PCT/US2014/036849 and WO 2013/026000 to Bryan; 2018/0127490 and 2018/0111984 to Bigal, et al.; 2018/0092899 to Liu, et al.; 2017/0240625 to Zeller, et al.; 2017/0342141 to Russo, et al.; 2018/0134772 to Sharma et al.; 2017/0201455 to Soares, et al.; 2017/0348303 to Bosse, et al.; 2017/0298115 to Loomis, et al.; and 2012/0294822 to Russo, et. al. 2018/0016647 and 2018/0016647 to Van Sinderen, et al.; 2018/0100169 to Soucaille, et al.; 2017/0232043 to Falb et al. and 2015/0045546 to Siksnys et al.: 2015/0216917 to Jones; 2015/0361436 to Hitchcock; 2015/0353901 to Liu; U.S. Pat. No. 9,131,884 to Holmes; 2015/0064138 to Lu; 2015/0093473 to Barrangou; 2012/0027786 to Gupta; 2015/0166641 to Goodman; 2015/0352023 to Berg.

In various aspects of the present invention, CRISPR is employed to modify aspects for both bacterial and helminthes gene expression such that undesired normally transcribed proteins are excised or precluded from being expressed, thus precluding the deleterious effects of such proteins. Thus, normally dangerous species of bacteria and helminthes (from a perspective of such bacteria or helminthes causing disease in a human) can be modified so that such undesired effects of bacterial and helminthes infection are disrupted or deleted or lessened in a fashion that still permits the beneficial aspects of bacterial and helminthes proteins to be maintained. Various embodiments of the present invention combine each of the above referenced four FLVR bacteria and using CRIPR, pathogenic and/or toxic elements are excised to preclude detrimental health issues that would normally be encountered using one or more of such bacteria, while preserving the immune system attributes attained by the presence of such bacteria. Preferably, the CRISPR modified bacteria of the FLVR species are then combined in a formulation suitable for use as either an oral composition (preferably administered via the strips as described herein).

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a new born or other individual. Thus, the various bacterial and helminthes species mentioned herein that are included in certain embodiments, may be modified using CRISPR methods to do one of several things, including adding antibiotic sensitivity to various species so that they can be employed for triggering immune responses of an individual, and then later killed or rendered ineffective by the use of targeted antibiotics or anti-helminthes drugs.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria. CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments includes making synthetic CRISPR-containing RNAs that target genes of interest and using them with Cas enzymes. The specificity of CRISPR-Cas systems permits one to design methods to target a single bacterial species so that only essential genes from that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is ~100 nt long.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modern word processors, Cas9 can be guided to specific locations within complex genomes by a short RNA search string. In certain embodiments, various particular bacterial species are focused on to delete or modulate their gene expressions. Together with modified bacteria (e.g. using a CRISPR system) certain embodiments include "cocktails" of beneficial bacteria selected from the group consisting of *Lactobacillus* sp., *Lactococcus* sp., *Bifidobacterium* sp., and *Streptococcus* sp. In some preferred embodiments the probiotic microorganism includes *Lactobacillus reuteri, Lactobacillus salivarius, Lactococcus lactis, Lactobacillus brevis, Lactobacillus rhamnosus, Lactobacillus aci-*

*dophilus, Lactobacillus plantarum, Lactobacillus casei, Lactobacillus paracasei*, and/or *Lactobacillus curvatus*.

In various embodiments, the CRISPR-Cas systems is employed to control the composition of the gut flora or oral microbiome, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

Controlling the composition of microbial populations is important in the context of desiring to expose individuals to particular species of bacterial and other microbes, helminthes, etc. and especially those that have not been previously exposed to antibiotics, antimicrobial peptides, and lytic bacteriophages. Use of CRISPR-Cas provides a generalized and programmable strategy that can distinguish between closely related microorganisms and allows for fine control over the composition of a microbial population for use in the present invention. Thus, the RNA directed immune systems in bacteria and archaea called CRISPR-Cas systems is employed in various embodiments of the present invention to selectively and quantitatively remove and/or alter individual bacterial strains based on sequence information to enable the fine tuning of exposure of desired antigens. Thus, such genome targeting using CRISPR-Cas systems allows one to specifically remove and/or alter individual microbial species and strains in desired ways.

In various embodiments, it is desirable to remove—using CRISPR-Cas systems—particular viable genes in pathogenic bacteria and/or other pathogenic portions (e.g plasmids, etc. of such bacteria)—while sparing other desired commensal bacteria, in order to provide exposure to desired immune developing proteins.

In various embodiments, one of skill in the art will appreciate that removal or alteration of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

Because certain embodiments relate to the modification of microbes—rather than to the human genome—and especially only those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Particular embodiments of the present invention are directed to the employment of four specific bacterial genera—*Lachnospira, Veillonella, Faecalibacterium* and *Rothia*. Modifying the human genome, made possible by the CRIPSR technique, has its own wonderful upsides and equally daunting downsides. Permanent deletion of genes from the human genome is much more controversial than deletion of bacterial genes. Thus, one desirable aspect of the present invention is directed to the far less controversial modification of gut microbes resident in the human being to promote health and to trigger the desired immune responses as described herein.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof, including the programmed triggering of particular immune responses in an infant. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, types of enhanced soils, etc. This permits labeling of living cells with a desired color.

Many embodiments rely upon the ability to deliver agents via mucosal adhesive strips, such as described, for example, in U.S. Pat. No. 8,701,671, which is fully incorporated herein by this reference. In such a manner, one objective is to accept the beneficial traits of the microbiome's interaction with the human immune system while avoiding the infectious aspects of bacterial, viral and helminth aspects of such exposure to a human being. Thus, in various embodiments of the present invention, the engineering of communal bacteria with improved properties using a CRISPR/Cas system is employed. Thus, in certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene.

There exist various concerns about how CRISPR-Cas systems and method will be employed with respect to attempting to improve human health through and using a technology that cuts sections of DNA out of a genome, effecting permanent changes to the human DNA. Indeed, many in the scientific community are considering whether a moratorium on the use of this powerful and yet simple technology should be implemented until such time as all the risks involved can be better assessed. In the context of the present invention, however, this particular issue is either absent or of lesser importance due to one focus of many embodiments being relegated to the modification of DNA of the microbe genomes, rather than the human genome. Thus, the present invention is one way in which the human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system. Moreover, the use of such a DNA modification system for microbes, but not for the direct deletion of genes from a human, and the use of such a system prior to the exposure of a human to such modified microbes, has not previously been done, especially with the added step of modifying select microbes having immune beneficial attributes—and especially using modified microbes that one would otherwise have considered to be pathogenic.

Individuals who have regular contact with livestock, such as farmers and their wives, have bacterial communities dominated by *Prevotella*, a type of bacteria that is also abundant in the gut microbiota of cattle and sheep. *Prevotella* are among the most numerous microbes culturable from the rumen and hind gut of cattle and sheep. Percentages vary but *Prevotella* is often the most common bacterial genus in the cattle. While certain aspects of particular embodiments are directed to the *Prevotella* genus, others are more focused on particular species within such genus, namely *P. intermedia*. The present inventors contend that the contributions of microbes to multiple aspects of human physiology and neurobiology in health and disease have up until now not been fully appreciated.

*Treponema denticola* is an oral anaerobic spirochete closely associated with the pathogenesis of periodontal disease—and the present inventors believe it is associated with numerous systemic diseases, including periodontitis and Alzheimer's disease. The *T. denticola* major surface protein (MSP), involved in adhesion and cytotoxicity, and the dentilisin serine protease are key virulence factors of this organism. Thus, one aspect of the present invention relates to the use of CRISPR-Cas or Cpf1 to target these virulence factors and thus, excise them from *T. denticola* so as to render it susceptible to antibiotics so as to reduce its presence in the oral microbiome, thus advancing the prevention of not only migraines, cluster headaches and dizziness, but for Alzheimer's disease as well. Periodontal diseases are polybacterially induced, multifactorial inflammatory processes of the tooth attachment apparatus and are the primary cause of tooth loss after the age of 35. The ability of such disease to escape detection and the failure of many to regularly visit a dentist to diagnose such a disease, leads to the prevalence of Alzheimer's disease as we see today. The elderly often show neglect of oral hygiene which can stimulate recurrent chronic oral infection, which promotes inflammation and then leads to confusion and dementia. Interfering with inflammation is thus one objective of the present invention and in certain embodiments, it is beneficial to combine anti-inflammatory agents with antibacterials.

The periodontopathogenic spirochete *T. denticola* possesses a number of virulence factors including motility, the ability to attach to host tissues, coaggregation with other oral bacteria, complement evasion mechanisms, and the presence of several outer sheath and periplasmic proteolytic and peptidolytic activities. Two components associated with the spirochetes' outer sheaths and extracellular vesicles are the major surface protein (also known as the major outer sheath protein [MSP]) and a serine protease, dentilisin, previously known as the chymotrypsin-like protease. Recent bioinformatics analysis reclassified dentilisin as a member of the subtilisin rather than the chymotrypsin family. Dentilisin is involved in the degradation of membrane basement proteins (laminin, fibronectin, and collagen IV), serum proteins (fibrinogen, transferrin, IgG, and IgA), including protease inhibitors (al-antitrypsin, antichymotrypsin, antithrombin, and antiplasmin), and bioactive peptides. Degradation of tight junction proteins by dentilisin seems to enable the penetration of epithelial cell layers by this oral spirochete. MSP is a major antigen with pore-forming activity. This abundant membrane protein mediates the binding of *T. denticola* to fibronectin, fibrinogen, laminin, and collagen, induces macrophage tolerance to further activation with lipopolysaccharide (LPS), and elicits cytotoxic effects in different cell types.

One object of the present invention is to employ LL-37 against *T. denticola*, especially employing the strips as set forth herein. Saliva inhibits dentilisin, attenuating its virulence properties but conserving LL-37 activity. Thus, one aspect of the present invention is directed to the use of LL-37 to kill *T. denticola*. The human host defense peptide LL-37 is preferably administered via the strips of the present invention, especially those having encapsulated pockets of the agent such that administration thereof can be achieved by the patient upon tongue pressure being applied to a frangible shell present as part of the strip. Deficiency in the human host defense peptide LL-37 has previously been correlated with severe periodontal disease. *Treponema denticola* is an oral anaerobic spirochete closely associated with the pathogenesis of periodontal disease. *Treponema denticola* is an important periodontal pathogen capable of tissue invasion. Its chymotrypsin-like proteinase (CTLP) can degrade a number of basement membrane components in vitro, thus suggesting a contribution to tissue invasion by the spirochete. Periopathogen survival is dependent upon evasion of complement-mediated destruction. *Treponema denticola*, an important contributor to periodontitis, evades killing by the alternative complement cascade by binding factor H (FH) to its surface.

In the healthy subgingival crevice, *Treponema denticola* account for ~1% of the total bacteria. With the progression of periodontitis, the abundance of oral treponemes increases dramatically and can reach 40% of the total bacterial population. Disease severity correlates specifically with the outgrowth of *Treponema denticola* and other bacterial species of the red microbial complex.

*Treponema denticolais* is an oral spirochete and periopathogen that transitions from low abundance in healthy subgingival crevices to high abundance in periodontal pockets. The *T. denticola* response regulator AtcR harbors the relatively rare, LytTR DNA binding domain. LytTR domain containing response regulators control critical transcriptional responses required for environmental adaptation. The functional diversity of the proteins encoded by the putative AtcR regulon suggests that AtcR sits at the top of a regulatory cascade that plays a central role in facilitating *T. denticola*'s ability to adapt to changing environmental conditions and thrive in periodontal pockets.

While most bacteria, including spirochetes, employ two component regulatory (TCR) systems and cyclic nucleotides to regulate adaptive responses, certain embodiments of the present invention are directed to the *T. denticola* genetic regulatory system and signaling mechanisms to decrease the growth and maintenance thereof in the oral cavity.

One general take-away from the present invention relates to how best to adopt practices that establish and retain and maintain oral health such that individuals do not suffer from the array of different maladies that are now understood to be related, whether directly or indirectly, to oral health. For example, it is common for individuals to get their teeth cleaned a few times a year. Upon such a cleaning procedure, however, the dental surfaces are relatively "clean" of the biofilms that where established thereon since the last dental cleaning visit. Instead of proactively applying a beneficial composition of beneficial bacteria to the cleaned surfaces, however, it is common and typical practice to simply have the dental patient leave the dental office, after scheduling another 6 month visit, and thus leave the colonization of the dental surfaces up to the chance presence of bacteria that may then be present in the person's mouth or surrounding environments. Given the growing and recent knowledge of the nature of oral biofilms, populated by a myriad of bacteria of different but coexisting species of bacteria, it is one aspect of the present invention to purposefully contact a person's recently cleaned teeth with a composition that contains bacteria believed to be especially beneficial to the establishment of a "healthy" biofilm. This entails, in certain embodiments, a progressive and successive contact of a person's teeth with different bacteria, with the staging of contact with various bacteria based upon the known synergistic relationship between oral bacteria, and with the emphasis being to limit the most pathogenic bacteria known to cause some of the prevalent problems suffered by humans.

The limitation of the growth and establishment of a certain spirochete, namely, *Treponema denticola*, is a focus of various embodiments. The use of CRISPR-Cas and similar technologies to alter the genetic makeup of such spirochete so as to lessen its infectivity in various regards is yet another way to accomplish this objective. Excision or retardation of the various virulence factors for this bacteria are other ways in which such a goal can be achieved. Still other ways to accomplish this objective involves interfering with the admittedly complex interactions and associations of other bacteria responsible for the growth of spirochetes in the oral cavity. Thus, by directly addressing still other supporting bacteria, one is able to indirectly, but nonetheless effectively, limit the progression of spirochetes, and in particular, *Treponema denticola*, establishment and growth. By doing so, one is saved from the ravages of Alzheimer's disease, as well as the several other diseases that are noted as being related to the oral health of a person. Providing a tooth contacting substance at the time of a dental cleaning is preferred, as well as possible re-applications of compositions by the individual so as to establish a preferred buildup of a beneficial biofilm having particular bacteria constituents. Such formulations for beneficial oral cavity health may vary dependent upon many factors, such as the particular diet of the individual, the race of the individual, the age, etc. It is known that bacterial populations vary greatly between individuals, as well as within the same individual based on health and age. Thus, selection of particular compositions having a pre-determined composition of bacteria formats and variety are contemplated by the present invention.

Bacterial species are able to use various energy sources, including light and diverse organic and inorganic chemicals, for growth and metabolism. These energy sources are used to produce an electrochemical gradient that provides an electron donor for metabolism and allows maintenance of a membrane potential and proton motive force. The energetics of living systems are driven by electron transfer processes in which electrons are transferred from a substrate, which is thereby oxidized, to a final electron acceptor, which is thereby reduced. In certain embodiments, it is possible to control metabolism by linking biochemical processes to an external electrochemical system, with such linking of biochemical and electrochemical systems permitting the use of electricity as a source of electrons for biotransformation reactions. A reversible biochemical-electrochemical link allows for conversion of microbial metabolic and/or enzyme catalytic energy into electricity.

In still other embodiments, employment of technology described in U.S. Pat. No. 9,131,884 to Holmes is employed to achieve desired further steps to address communication of biological disease status to a third party. For example, in certain embodiments, a medical device is associated with a mucosal strip that comprises a microarray having a bioactive agent capable of interacting with a disease marker biological analyte and a reservoir having at least one therapeutic agent, with the device able to release the therapeutic agent(s) from the medical device. In certain embodiments, at least two microchips with a microarray scanning device adapted to obtain physical parameter data of an interaction between the disease marker biological analyte and the bioactive agent is employed. A biometric recognition device is configured to compare the physical parameter data with an analyte interaction profile. The therapeutic agent releasing device controls the release of the therapeutic agent from the reservoir. The interface device facilitates communications between the microarray scanning device, biometric recognition device and the therapeutic agent releasing device. An energy source to power the medical device can take several forms, including biologically activated batteries that are preferably associated with the strip.

In certain other embodiments, sugar is used as a source of energy, notably glucose that is converted into different sugars via an enzymatic cascade to provide necessary energy to create an electrochemical gradient. This, in turn, is used to power an enzyme that synthesizes adenosine triphosphate (ATP). In contrast to natural catabolic pathways for cellular glucose oxidation, a preferred embodiment does not rely on ATP as an energy carrier. Instead, two redox enzymes oxidize glucose, generating reduced nicotinamide adenine dinucleotide (NADH) as the sugar is broken down. Another series of enzymes (as many as ten additional enzymes) further breakdown the sugars and feed them back to the redox enzymes to produce more NADH, with water and carbon dioxide being the only by-products. NADH is a reducing agent and acts as an electron shuttle that carries electrons in living cells from one molecule to another. NADH first transfers the electrons stripped from the glucose to a mediator with the help of an enzyme. The mediator then delivers these electrons to the battery's electrode, rendering it available to power an electronic device. Such a battery mimics the way a living cell transfers electrons from one molecule to another to generate power, it runs on renewable sugars, and has a high-energy storage density, rechargeable providing an additional sugar solution. Malodextrin—a polymer made up of glucose subunits—may be employed together with particular different enzymes able to strip electrons from a single glucose molecule, thus harnessing the generated energy to power an electrical device.

Certain embodiments of the present invention are directed to a method for reducing the likelihood of developing dental caries and halitosis, comprising providing to an oral cavity of an individual subject a first bacterial composition comprising beneficial bacteria adapted to form a biofilm, such beneficial bacteria comprising a bacterium of the genus *Rothia*. Preferably, the bacterial composition does not inhibit growth of a bacterium of species *Lactobacillus salivarius*. A further step of such method is to topically administer to the individual subject a second composition comprising: an oral probiotic comprising at least two of the following bacteria: *Lactobacillus brevis* CD2, *Streptococcus sanguinis* BCC23, *Lactobacillus acidophilus, Lactobacillus bulgaricus, Lactobacillus johnsonii, Bifidobacterium bifidum, Enterococcus faecium, Lactobacillus acidophilus, Lactobacillus rhamnosus, Lactobacillus plantarum, Lactobacillus reuteri, Lactobacillus paracasei, Lactobacillus casei, Lactobacillus casei* strain Shirota, *Lachnospira, Veillonella, Faecalibacterium* and *Prevotella*; at least one zinc-based compound selected from the group consisting of zinc acetate, zinc chloride, zinc citrate, and zinc sulphate; and at least one bioactive flavonoid selected from the group consisting of baicalein, naringenin, catechins, the product maritime pine bark extracts sold under the trademark Pycnoqenol™, quercetin, trans-resveratrol, luteolin, kaempferol, hesperidin, hesperetin, naringin, diosmin, rutin, nobiletin, and tangeretin.

Preferably, the step of topically administering comprises providing the second composition in the form of one of a toothpaste, mouth wash, gargle solution, nose spray, mouth spray, throat spray, chewing gum, hydrogel, oral strip, and/or oral cream. In certain embodiments, a bioadhesive strip is used that has a first and second side, with its first side having at least one encapsulated feature containing the second composition., with such strip preferably being dissolvable in a person's mouth.

In other embodiments, using a clustered regularly interspaced short palindromic repeats (CRIPSR)-CRISPR associated protein (Cas) system or a CRISPR from *Prevotella* and Franscisella 1 (Cpf1a) system, one selectively kills pathogenic bacteria in the individual subject's oral cavity. In still other embodiments, at least one bacteria is employed that has been modified by employment of a CRISPR-Cas or Cpf1 system to remove a virulence factor selected from the group consisting of gelatinase and hemolysin. In preferred embodiments, the first bacterial composition is administered after the individual subject has cleaned their teeth, thus removing biofilms pre-existing in the individual's mouth. Preferred embodiments also include a second composition that includes xylitol and *Veillonella* bacteria. While most of the discussion herein is directed to use by human's it should be understood that other mammals, especially companion pets, such as dogs and cats can benefit from the present invention.

While not bound by theory, it is believed that the administration of the above referenced second composition acts to lower the pH of an individual subject's oral cavity in an amount sufficient to disrupt the formation of biofilms by pathogenic bacteria, thus reducing caries and halitosis. Certain embodiments further focus on the reduction or killing of certain pathogenic bacteria that generate volatile sulfur compounds, such as methylmercaptan and hydrogen sulfite, and specifically the pathogenic bacteria *Porphyromonas gingivalis*, which is also associated with Alzheimer's disease.

It will be understood that in various embodiments of the present invention, one or more of live or dormant bacteria, heat-kill bacteria, or bacterial post-biotics may be employed to achieve particular desired aspects of reducing the likelihood of caries and/or halitosis in the oral cavity. In particular, certain aspects of various embodiments include the use of dormant (e.g. lyophilized, freeze dried) bacteria as a way to achieve desired stabilization of certain bacteria for the purposes of extending shelf-life and/or to ensure delivery of such bacteria to a target tissue where they may then be restored to a metabolically active state. Thus, various aspects of the present invention extend to areas involving the manufacturing and packaging of bacterial comprising products so as to preserve desired biological attributes when administered to an individual subject. Similarly, heat-treated probiotic cells, cell-free supernatants, and purified key components are provided in a manner so as to confer beneficial effects by delivering compounds or mixtures of bacterial components and/or formulations to achieve a desired effect, such as immunomodulatory, bactericidal to pathogenic species, disruptive to biofilms, cross-feeding to support other beneficial species, anti-inflammatory, and triggers to achieve beneficial host responses. Thus, it should be understood that in certain embodiments, not all of the bacteria employed may be "live" in the state they are in when purchased or provided to an individual for use. The provision of dormant bacteria, heat-kill bacteria, or bacterial post-biotics, including metabolites associated therewith, should therefore be understood to be part of the various embodiments of the inventions as described herein and the references incorporated herein by reference provides ample guidance to one of skill in the art to address manufacturing, production and shelf-life concerns.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for reducing the likelihood of developing dental caries and halitosis, comprising:
   providing to an oral cavity of an individual subject a first bacterial composition comprising beneficial bacteria adapted to form a biofilm, said beneficial bacteria comprising a bacterium of the genus *Rothia*, and wherein said bacterial composition does not inhibit growth of a bacterium of species *Lactobacillus salivarius;*
   topically administering to the individual subject a second composition comprising:
   an oral probiotic comprising at least two of the following bacteria: *Lactobacillus brevis* CD2, *Streptococcus sanguinis* BCC23, *Lactobacillus acidophilus, Lactobacillus bulgaricus, Lactobacillus johnsonii, Bifidobacterium bifidum, Enterococcus faecium, Lactobacillus acidophilus, Lactobacillus rhamnosus, Lactobacillus plantarum, Lactobacillus reuteri, Lactobacillus paracasei, Lactobacillus casei, Lactobacillus casei* strain Shirota, *Lachnospira, Veillonella, Faecalibacterium* and *Prevotella;*
   at least one zinc-based compound selected from the group consisting of zinc acetate, zinc chloride, zinc citrate, and zinc sulphate; and at least one bioactive flavonoid selected from the group consisting of baicalein, naringenin, catechins, quercetin, trans-resveratrol, luteolin, kaempferol, hesperidin, hesperetin, naringin, diosmin, rutin, nobiletin, and tangeretin.

2. The method of claim 1, wherein the step of topically administering comprises providing said second composition in the form of one of a toothpaste, mouth wash, gargle solution, nose spray, mouth spray, throat spray, chewing gum, hydrogel, oral strip, oral cream, extruded chew and jerky chew.

3. The method of claim 1, wherein the step of topically administering comprises providing to the individual subject a bioadhesive strip, said strip having a first and second side, said first side having at least one encapsulated feature containing said second composition.

4. The method as set forth in claim 1, wherein said strip is dissolvable in the individual subject's mouth.

5. The method of claim 1, further comprising, using a clustered regularly interspaced short palindromic repeats (CRIPSR)-CRISPR associated protein (Cas) system or a CRISPR from *Prevotella* and Franscisella 1 (Cpf1a) system, selectively killing pathogenic bacteria in the individual subject's oral cavity.

6. The method of claim 1, wherein said step of providing the first bacterial composition is performed after the individual subject has cleaned their teeth.

7. The method as set forth in claim 1, wherein said second composition further includes xylitol.

8. The method of claim 1, wherein said second composition comprises *Veillonella* bacteria.

9. The method of claim 3, wherein said strip further comprises breath freshening components.

10. The method as set forth in claim 1, further comprising providing at least one bacteria that has been modified by employment of a CRISPR-Cas or Cpf1 system to remove a virulence factor selected from the group consisting of gelatinase and hemolysin.

11. The method as set forth in claim 1, wherein the individual subject is a human.

12. The method as set forth in claim 1, wherein the individual subject is a canine.

13. The method as set forth in claim 1, wherein the oral probiotic lowers the pH of the individual subject's oral cavity in an amount sufficient to disrupt the formation of biofilms by pathogenic bacteria.

14. A method for reducing the likelihood of developing dental caries and halitosis, comprising:
providing to an oral cavity of an individual subject a first bacterial composition comprising beneficial bacteria adapted to form a biofilm, said beneficial bacteria comprising a bacterium of the genus *Rothia*, and wherein said bacterial composition does not inhibit growth of a bacterium of species *Lactobacillus salivarius*; said step of providing performed after the individual subject has cleaned their teeth;
topically administering to the individual subject a second composition comprising:
an oral probiotic comprising at least two of the following bacteria: *Lactobacillus brevis* CD2, *Streptococcus sanguinis* BCC23, *Lactobacillus acidophilus*, *Lactobacillus bulgaricus*, *Lactobacillus johnsonii*, *Bifidobacterium bifidum*, *Enterococcus faecium*, *Lactobacillus acidophilus*, *Lactobacillus rhamnosus*, *Lactobacillus plantarum*, *Lactobacillus reuteri*, *Lactobacillus paracasei*, *Lactobacillus casei*, *Lactobacillus casei* strain Shirota, *Lachnospira*, *Veillonella*, *Faecalibacterium* and *Prevotella*;
at least one zinc-based compound selected from the group consisting of zinc acetate, zinc chloride, zinc citrate, and zinc sulphate; and
at least one bioactive flavonoid selected from the group consisting of baicalein, naringenin, catechins, quercetin, trans-resveratrol, Luteolin, kaempferol, hesperidin, hesperetin, naringin, diosmin, rutin, nobiletin, and tangeretin; and
using a clustered regularly interspaced short palindromic repeats (CRIPSR)-CRISPR associated protein (Cas) system or a CRISPR from *Prevotella* and Franscisella 1 (Cpf1a) system, selectively killing pathogenic bacteria in the individual subject's oral cavity.

15. The method as set forth in claim 14, wherein said pathogenic bacteria generate volatile sulfur compounds comprising one of methylmercaptan and hydrogen sulfite.

16. The method as set forth in claim 14, wherein said pathogenic bacteria is *Porphyromonas gingivalis*.

17. The method as set forth in claim 1, wherein the individual subject is a human.

18. The method as set forth in claim 1, wherein the individual subject is a canine.

19. A method for reducing the likelihood of developing dental caries and halitosis, comprising:
providing to an oral cavity of an individual subject a first bacterial composition comprising beneficial bacteria adapted to form a biofilm, said beneficial bacteria comprising a bacterium of the genus *Rothia*, and wherein said bacterial composition does not inhibit growth of a bacterium of species *Lactobacillus salivarius*; said step of providing performed after the individual subject has cleaned their teeth;
topically administering to the individual subject a second composition comprising:
an oral probiotic comprising at least two of the following bacteria: *Lactobacillus brevis* CD2, *Streptococcus sanguinis* BCC23, *Lactobacillus rhamnosus*, *Lactobacillus plantarum*, *Lactobacillus reuteri*, *Lactobacillus casei* strain Shirota, and *Veillonella*;
at least one zinc-based compound selected from the group consisting of zinc acetate, zinc chloride, zinc citrate, and zinc sulphate; and
at least one bioactive flavonoid selected from the group consisting of quercetin, nobiletin, tangeretin; and xylitol.

20. The method of claim 1, wherein the step of topically administering comprises providing said second composition in the form of one of a toothpaste, mouth wash, gargle solution, nose spray, mouth spray, throat spray, chewing gum, hydrogel, oral strip, and oral cream.

* * * * *